(12) United States Patent  
Buist et al.

(10) Patent No.: US 7,169,383 B1  
(45) Date of Patent: Jan. 30, 2007

(54) ATTACHING SUBSTANCES TO MICRO-ORGANISMS

(75) Inventors: Girbe Buist, Groningen (NL); Cornelis Johannes Leenhouts, Haren (NL); Gerard Venema, Haren (NL); Jan Kok, Groningen (NL)

(73) Assignee: Applied Nanosystems B.V., Groningen (NL)

( * ) Notice: Subject to any disclaimer, the term of this patent is extended or adjusted under 35 U.S.C. 154(b) by 0 days.

(21) Appl. No.: 09/554,354

(22) PCT Filed: Nov. 12, 1998

(86) PCT No.: PCT/NL98/00655

§ 371 (c)(1),  
(2), (4) Date: Jun. 19, 2000

(87) PCT Pub. No.: WO99/25836

PCT Pub. Date: May 27, 1999

(30) Foreign Application Priority Data

Nov. 13, 1997 (EP) .................................. 97203539

(51) Int. Cl.  
*A01N 63/00* (2006.01)  
*A01N 65/00* (2006.01)

(52) U.S. Cl. .................. 424/93.1; 424/93.2; 424/93.4; 424/93.45

(58) Field of Classification Search ............... 424/93.1, 424/93.2, 93.4, 93.45  
See application file for complete search history.

(56) References Cited

U.S. PATENT DOCUMENTS 5,616,686 A    4/1997   Fischetti

FOREIGN PATENT DOCUMENTS

| WO | 9418330 | 8/1994 |
| WO | 9509232 | 4/1995 |
| WO | 9531561 | 11/1995 |
| WO | 9708553 | 3/1997 |

OTHER PUBLICATIONS

Rielinger et al. *Peptide Hormones* University Park Press pp. 1-7, 1976.*

Hahn et al (Behring Institute Mitteilungen vol. 0 No. 98, pp. 315-325), 1997.*

Haddad et al (FEMS Immunology and Medical Microbiology vol. 12, No. 3-4, Dec. 1995, pp. 175-185).*

Hess et al., *Listeria monocytogenes* p60 Supports Host Cell Invasion by and In Vivo Survival of Attenuated *Salmonella typhimurium*, Infection and Immunity, May 1995, pp. 2047-2053, vol. 63, No. 5.

J. Piard et al.; Cell Wall Anchoring of the Streptococcus Pyogenes M6 Protein in various Lactic Acid Bacteria; 6001 Chemical Abstracts, Columbus Ohio, USA, vol. 127 (1997) Jul. 21, No. 3, p. 341.

P. Vijaykumar et al.; Identification of an Endogenous Membrane anchor-cleaving Enzyme for Group A Streptococcal M Protein; 6001 Chemical Abstracts, Columbus, Ohio, USA, vol. 112, Feb. 12, 1990, No. 7, p. 391.

C. Atkinson et al.; Is There Evidence for a Common Amino Acid Sequence of Proteins with Membrane Attaching Ability?; 6001 Chemical Abstracts, Columbus Ohio, USA; vol. 106, Mar. 30, 1987 No. 13, p. 282.

G. Buist, et al.; Molecular Cloning and Nucleotide Sequence of The Gene Encoding the Major Peptidoglycan Hydrolase of Lactococcus Lactis, a Muramidase Needed for Cell Separation; 6001 Chemical Abstracts, Columbus, Ohio, USA. vol. 123, Aug. 28, 1995, No. 9, p. 530.

G. Buist et al.; The N-acetylmuramidase of *Lactocossus lactis* Binds to the Cell Wall by Means of Repeated Motifs Located in the C-terminal Domain; Vertrouwelkji, Department of Genetics Biological Center; Dec. 12, 1997; pp. 1-20.

S. Stahl et al.,; Bacterial Surface Display: Trends and Progress; Elsevier Science Ltd.; Tibtech May 1997 vol. 15, pp. 185-192.

S.Altschul et al.; Basic Local Alignment Search Tool; J.Mol.Biol. 1990; 215. pp. 403-410.

R. Baankreis; The Role of Lactococcal Peptidases in Cheese Ripening; Academic Thesis; 1992; pp. 109-111.

C.Beliveau et al.; Cloning, Sequencing, and Expression in *Escherichia coli* of a *Streptococcus faecalis* Autolysin; Journal of Bacteriology, Sep. 1991; vol. 173, No. 18, pp. 5619-5623.

N.Birkeland; Cloning, Molecular Characterization, and Expression of the Genes Encoding The Lytic Functions of Lactococcal Bacteriophage OLC3: a Dual Lysis System of Modular Design; Can.J.Microbiol. vol. 40, 1994; pp. 658-665.

G. Buist et al.; Autolysis of *Lactococcus lactis* Caused by Induced Overproduction of Its Major Autolysis, AcmA; Applied and Environmental Microbiology, Jul. 1997, vol. 63, No. 7, pp. 2722-2728.

(Continued)

*Primary Examiner*—Mark Navarro  
(74) *Attorney, Agent, or Firm*—TraskBritt

(57) ABSTRACT

The invention relates to surface display of proteins on micro-organisms via the targeting and anchoring of heterologous proteins to the outer surface of cells such as yeast, fungi, mammalian and plant cells, and bacteria. The invention provides a proteinaceous substance comprising a reactive group and at least one attaching peptide which comprises a stretch of amino acids having a sequence corresponding to at least a part of the consensus amino acid sequence listed in FIG. 10 and comprises a method for attaching a proteinaceous substance to the cell wall of a micro-organism comprising the use of said attaching peptide.

11 Claims, 12 Drawing Sheets

OTHER PUBLICATIONS

Figure 1:
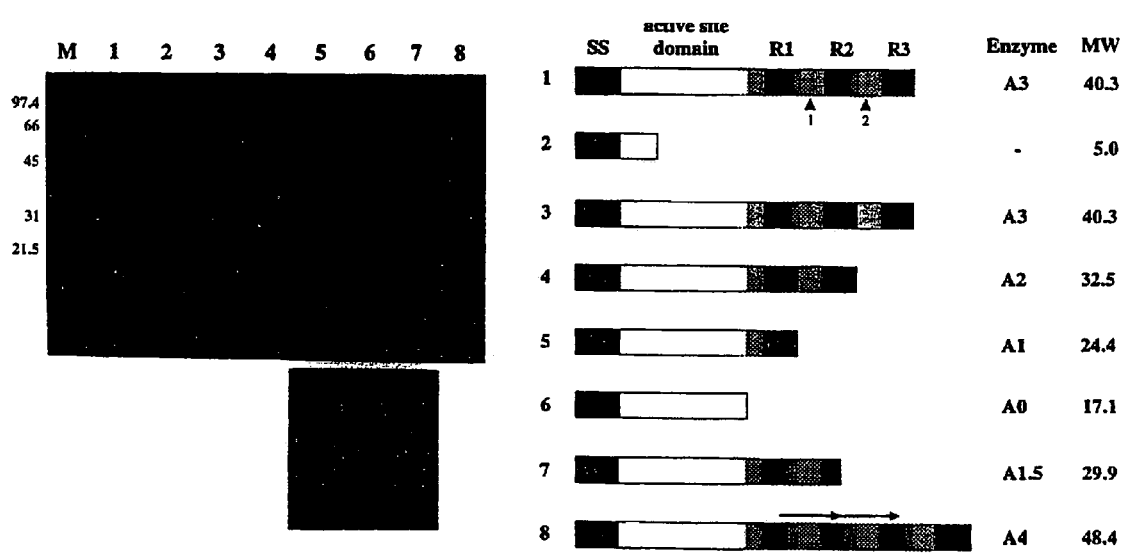

G. Buist et al.; Molecular Cloning and Nucleotide Sequence of the Gene Encoding the Major Peptidoglycan Hydrolase of *Lactococcus lactis*, a Muramidase Needed for Cell Separation; Journal of Bacteriology, Mar. 1995, vol. 177, No. 6 pp. 1554-1563.

J. Garcia, et al.; Carboxy-Terminal Deletion Analysis of the Major Pneumococcal Autolysin; Journal of Bacteriology, Jul. 1994, vol. 176, No. 13, pp. 4066-4072.

M. Gasson; Plasmid Complements of *Streptococcus lactic* NCDO 712 and Other Lactic Streptococci After Protoplast-Induced Curing; Journal of Bacteriology, Apr. 1983, vol. 154, No. 1, pp. 1-9.

M. Hourdou, et al.; Characterization of the Sporulation-related γ-D-glutamyl-(L)mesodiaminopimelic-acid-hydrolysing Peptidase I of *Bacillus sphaericus* NCTC 9602 as a Member of the Metallo(zinc) carboxypeptidase A Family; Biochem. J. 1993 292, pp. 563-570.

B.Joris et al.; Modular Design of the *Enterococcus hirae* Muramidase-2 and *Steptococcus faecalis* Autolysin; TEMS Microbiology Letters 91 (1992) pp. 257-264.

R. Kariyama, et al.; Extracellular and Cellular Distribution of Muramidase-2 and Muramidase-1 of *Enterococcus hirae* ATCC 9790; Journal of Bacteriology, May 1992, vol. 174, No. 10, pp. 3236-3241.

J. Knowles, et al.; Cellulase Families and Their Genes; Tibtech-Sep. 1987 vol. 5, pp. 255-261.

K. Kuroda et al.; Cloning, Sequencing and Genetic Mapping of a *Bacillus subtilis* cell Wall Adrolase Gene; Journal of General Microbiology 1990, 136; pp. 2209-2216.

A. Kuroda et al; Genetic Structure, Isolation and Characterization of a *Bacillus lickeniformis* Cell Wall Hydrolase; Mol Gen Genet 1992 234; pp. 129-137.

U.Laemmli; Cleavage of Structural Proteins During the Assembly of the Head of baceriophage T4; Nature vol. 224; Aug. 15, 1970; pp. 680-685.

K. Leenhouts et al; Molecular Cloning and Expression in Lactococcus; Med. Fac. Landbouww.Univ.Gent. 57/4b, 1992; pp. 2031-2043.

P.Langchamp et al; Lytic enzymes associated with defective prophages of *Bacillus subtilis*: sequencing and characterization of the region comprising the N-acetylmuramoyl-l-alanine amidase gene of prophage PBSX; Microbiology 1994, 140; pp. 1855-1867.

R. Lopez et al; Architecture and Domain Interchange of the Pneumococcal Cell Wall Lytic Enzymes; Dev.Biol.Stand. Basel, Karger 1995; vol. 85; pp. 273-281.

Y. Oda; et al.; Molecular Cloning, Sequence Analysis, and Characterization of a New Cell Wall Hydrolase, CwlL, of *Bacillus licheniformis*; Mol Gen Genet 1993, 241; pp. 380-388.

T.Oshida, et al; *A Staphylococcus aureus* autolysin That has an N-acetylmuramoyl-L-alanine amidase Domain and an Endo-β-N-acetylglucosaminidase Domain: Cloning, Sequence Analysis, and Characterization; Proc.Natl.Acad.Sci, USA; vol. 92 Jan. 1995; pp. 285-289.

G. Perez-Martinez, et al; Protein Export Elements from *Lactococcus lactis*; Mol Gen Genet 1992 234; pp. 401-411.

C.Potvin, et al; Cloning, Sequencing and Expression of a *Bacillus* Bacteriolytic Enzyme in *Escherichia coli*; Mol Gen Genet 1988 214; pp. 241-248.

M.Rashid, et al; Glucosaminidase of *Bacillus subtilis*: Cloning Regulation, Primary Structure and Biochemical Bachteization; Microbiology 1995, 141, pp. 2391-2404.

G. Ruhland et al; Cell-surface Location of *Listeria*-specific protein p60-Detection of *Listera* Cells by Indirect Immunofluorescence; Journal of General Microbiology 1993, 139, pp. 609-616.

J.Sambrook et al; Molecular Cloning, a Laboratory Manual, Second Edition; Cold Spring Harbor Laboratory Press 1989; Table of Contents.

F. Sanger et al; DNA Sequencing with Chain-terminating Inhitibors; Proc.Natl.Acad.Sci.USA; vol. 74, No. 12 Dec. 1977; pp. 5463-5467.

J.Sanz et al; Construction of a Multifunctional Pneumococcal Murein Hydrolase by Module Assembly; Eur.J.Biochem. 235, 1996; pp. 601-605.

M.Sheehan, et al; Analysis of the catalytic Domain of the Lysin of the Lactococcal bacteriophage Tuc2009 by Chimeric Gene Assembling; FEMS Microbiology Letters 140 1996; pp. 23-28.

H.Smith, et al; Construction and Use of Signal Sequence Selection Vectors in *Escherichia coli* and *Bacillus subtilis*; Journal of Bacteriology, Jul. 1987, pp. 3321-3328.

F.Studier, et al.; Use of T7RNA Polymerase to Direct Expression of Cloned Genes; Methods in Enzymology, vol. 185 Academic Press, Inc. 1990; pp. 60-89.

H.Towbin et al; Electrophoretic Transfer of Proteins from Polyacrylamide Gels to Nitrocellulose Sheets: Procedure and Some Applications; Proc. Natl.Acad.Sci USA; vol. 76, No. 9, Sep. 1979 pp. 4350-4354.

M.van de Guchte et al; Heterologous Gene Expression in *Lactococcus lactis* subsp. *Lactis*: Synthesis, Secretion, and Processing of the *Bacillus subtilis* Neutral Protease; Applied and Environmental Microbiology, Sep. 1990; pp. 2602-2611.

J.Maarten van Dijl, et al.; Signal Peptidase I of *Bacillus subtilis*: Patterns of Conserved Amino Acids in Prokaryotic and Eukaryotic Type I Signal Peptidases; The EMBO Journal, vol. 11, No. 8; 1992; pp. 2819-2828.

A.Vasala, et al.; Genetic and Biochemical Characterization of the *Lactobacillus delbrueckii* subsp. *Lactis* bacteriophage LL-H Lysin; Applied and Environmental Microbiology, No. 1995; pp. 4004-4011.

J. Vieira et al.; Short Communications New pUC-derived Cloning Vectors with Different Selectable Markers and DNA Replication Origins; Gene. 100 1991, pp. 189-194.

R.Wilson, et al; 2.2 Mb of Contiguous Nucleotide Sequence from Chromosome III of C. elegans; Nature, vol. 368, Mar. 3, 1994; pp. 32-38.

E. Zabarovsy, et al.; High Efficiency Electroporation of Ligated DNA into Bacteria; Nucleic Acids Research, No. 18, No. 19; 1990; p. 5912.

S. Stahl et al.; Bacterial Surface Display: Trends and Progress; Tibtech May 1997, vol. 15; pp. 185-192.

D.Medaglini et al; Mucosal and Systemic Immune Responses to a Recombinant Protein Expressed on the Surface of the Oral Commensal Bacterium *Streptococcus gordonii* After Oral Colonization; Proc. Natl.Acad. Sci.UISA, vol. 92, Jul. 1995; pp. 6868-6872.

K.Robinson et al.; Oral Vaccination of Mice Against Tetanus with Recombinant *Lactococcus lactis*; Nature Biotechnology, vol. 15 Jul. 1997; pp. 653-657.

Bateman et al., The Structure of a LysM Domain from *E. coli* Membrane-bound Lytic Murein Transglycosylase D (MliD), J. Mol. Biol., 2000, pp. 1113-1119, vol. 299.

Steen et al., Cell Wall Attachment of a Widely Distributed Peptidoglycan Binding Domain Is Hindered by Cell Wall Constituents, The Journal of Biological Chemistry, 2003, pp. 23874-23881 vol. 278,. No. 20.

\* cited by examiner

S  CW  CY  MB  M      S  CW  CY  MB  M pGBL1                    pGBLR

FIG. 10

```
R1  TTYTVKSGDTLWGISQRYGISVAQIQSANNLKSTIIYIGQKLVLT      243-287    (SEQ ID NO:14)
R2  TTVKVKSGDTLWALSVKYKTSIAQLKSWNHLSSDTIYIGQNLIVS      319-363    (SEQ ID NO:15)
R3  SIHKVVKGDTLWGLSQKSGSPIASIKAWNHLSSDTILIGQYLRIK      393-437    (SEQ ID NO:16)
     . .  *  ****** . *      *.   .* . *.*.**. * *  .. 
```

Consensus:

```
Yx [V] Kx [G][D] T  Lxx [I] Axxxxxxxxxxxxx Lxxx [N]  x[x] [L] xxxxx[x] [I] [V]  xx [G] Qx [I] [L] x   (SEQ ID NO:17)
H  [I] R  [E]  S       [V]              S                    [I]            [L]                [V] [I]  (SEQ ID NO:17)
   [L]                 [I]              I                                         [V]           [I] [L] (SEQ ID NO:17)
```

Figure 11

Fig. 11 continued

```
Caenorhabditis elegans    TEIKSGDSCWNIASNAKISVERLQQLN KGNKCDKLPLGDKLCLA              23- 66(11)
                          LKLKAEDTCFKIHSSQKLSERQFLGNH EGNDCDKLKVGKEVCVA              78-121(21)
                          HKIQKGDTCFKIWTTNKISEKQFRNLN KGLDCDRLEIGKEVCIS             143-186(22)
                          LRIKEGDTCYNIWTSQKISEQEFHELN KGLDCDKLEIGKEVCVT             208-251(19)
                          YRFKKGDTCYKIWTSKHSEKQFRALN  RGIDCDRLVPGKELCVG             271-314(20)
                          ITVKPGDTCFSIWTSQRHTQQQFHDIN PELDCDKLEIGKEVCVT             335-378(23)
                          VKIHPGDTCFHIWTSQRHTQQQFHDLH KRLDCDRLEVGKEVCVT             402-445(21)
                          VQINPGDTCFKIWSAQKLTEQQFIELN KGLDCDRLEVGKEVCIA             467-510(37)
                          TEVKEGDTCFKIWSAHKITEQQFMERN RGLDCNRLEVGKEVCIV             548-591(44)
                          INVKEGDTCFKIWSAQEHTEQQFHEAN RGLDCNKLAVGKEVCVS             636-679(66)      1614   U64836   PUTATIVE ENDOCHITINASE
                          ATITPGNTCFNISVAYGINLT    DLQ KTYDCKALEVGDTICVS             746-786(8)
                          IEVIKGDTCHFLENAFKTNQTEHERAN EGVKCDNLPIGRHNCVW              795-838

Caenorhabditis elegans    HTIKSGDTCWKIASEASISVQELEQLN SRKSFAILAVGLSEQEF              23- 66(51)
                          IHVKEGDTCYTIWTSQHLTEKQFHDRN EELNCRHLEIGHEVCVD             118-161(25)      1JB4   I70858   PUTATIVE ENDOCHITINASE
                          ATVPGSSCYTISASYGLNLAELQTTY  HCDALQVDDTICVS                187-226(9)
                          IEILNGDTCGFLENAFQTNNTENEIAH EGVKCDNLPIGRHHCVW              236-279

Bacillus subtilis    eee  HTVQRKETLYRISNKYVKSRTGEEKIRAVNHLNGRIDVYTGQVLDIP              191-136           240    L47648
Citrobacter freundii eae  YTLKTGESVAQLSKSQGISVPVIWSLHKHLYSSESENNKASPGQQIILP             65-113            936    Q07591
Escherichia coli     ymeA YLATGETVADLSKSQDINLSTIHSLNKHLYSSESERNKAAPGQQIILP              65-113            934    P43261
Bacillus subtilis    ymeA IEVQGQDTLMSIADQVADTRKINKRDFIEWVADRNQLQTSDIQPGDELVIP           40- 90            105    Z73234
Streptococcus pyogenes    YTVKYGDTLSTIAEANGIDVHVLGDINHIANIDLIFPDTILTANYNQRGQATTLT       47-103            339    U09352
Bacillus subtilis    yqbp YTVKKGDTLMDIAGRFIGNSTQMPKIMNANKTAMIKRSKRNIRQPGHMIFPGQKLKIP    177-234           235    G1225954
Bacillus subtilis         YTVKKGDTLMDLAGKFYGDSTRMRKIHKVNRKAMIKRSKRNIRQPGHMIFPQQKLKIP    161-218           219    P45932
```

ATTACHING SUBSTANCES TO MICRO-ORGANISMS

Heterologous surface display of proteins (Stahl and Uhlen, TIBTECH May 1997, 15±185–192) on recombinant micro-organisms via the targeting and anchoring of heterologous proteins to the outer surface of host-cells such as yeast, fungi, mammalian and plant cells, and bacteria has been possible for several years. Display of heterologous proteins at the surface of these cells has taken many forms, varying from the expression of reactive groups such as antigenic determinants, heterologous enzymes, (single-chain) antibodies, polyhistidyl tags, peptides, and other compounds. Heterologous surface display has been applied as a tool for applied and fundamental research in microbiology, molecular biology, vaccinology and biotechnology, and several patent applications have been filed.

Yet another application of bacterial surface display has been the development of live-bacterial-vaccine delivery systems. The cell-surface display of heterologous antigenic determinants has been considered advantageous for the induction of antigen-specific immune responses when using live recombinant cells for immunisation. Another application has been the use of bacterial surface display in generating whole-cell bioadsorbents or biofilters for environmental purposes, microbiocatalysts, and diagnostic tools.

In general, one has used chimeric proteins consisting of an anchoring or targeting part specific and selective for the recombinant organism used and has combined this part with a part comprising a reactive group as described above. A well known anchoring part for example comprise the so-called LPXTG box, that binds covalently to a *Staphylococcus* bacterial surface, i.e. in the form of a fully integrated membrane protein. In this way, chimeric proteins are composed of at least two (poly)peptides of different genetic origin joined by a normal peptide bond. For example, in patent application WO 94/18830 relating to the isolation of compounds from complex mixtures and the preparation of immobilised ligands (bioadsorbents), a method has been claimed for obtaining such a ligand which comprises anchoring a binding protein in or at the exterior of the cell wall of a recombinant cell. Said binding protein is essentially a chimeric-protein produced by said recombinant cell, and is composed of an N-terminal part, derived from for example an antibody, that is capable of binding to a specific compound joined with a C-terminal anchoring part, derived from an anchoring protein purposely selected for being functional in the specific cell chosen. In patent application WO 97/08553 a method has been claimed for the targeting of proteins selectively to the cell wall of *Staphylococcus* spp, using as anchoring proteins long stretches of at least 80–90 amino acid long amino acid cell wall-targeting signals derived from the lysostaphin gene or amidase gene of *Staphylococcus* which encode for proteins that selectively bind to *Staphylococcus* cell wall components.

Vaccine delivery or immunisation via attenuated bacterial vector strains expressing distinct antigenic determinants against a wide variety of diseases is now commonly being developed. Recently, mucosal (for example nasal or oral) vaccination using such vectors has received a great deal of attention. For example, both systemic and mucosal antibody responses against an antigenic determinant of the hornet venom were detected in mice orally colonised with a genetically engineered human oral commensal *Streptococcus gordonii* expressing said antigenic determinant on its surface (Medaglini et al., PNAS 1995, 2; 6868–6872). Also, a protective immune response could be elicited by oral delivery of a recombinant bacterial vaccine wherein tetanus toxin fragment C was expressed constitutively in *Lactococcus lactis* (Robinson et al., Nature Biotechnology 1997, 15; 653–657). Especially mucosal immunisation as a means of inducing IgG and secretory IgA antibodies directed against specific pathogens of mucosal surfaces is considered an effective route of vaccination. Immunogens expressed by bacterial vectors are presented in particulate form to the antigen-presenting cells (for example M-cells) of the immune system and should therefore be less likely to induce tolerance than soluble antigens. In addition, the existence of a common mucosal immune system permits immunisation on one specific mucosal surface to induce secretion of antigen-specific IgA, and other specific immune responses at distant mucosal sites. A drawback to this approach is the potential of the bacterial strain to cause inflammation and disease in itself, potentially leading to fever and bacteraemia. An alternative approach avoids the use of attenuated bacterial strains that may become pathogenic themselves by choosing recombinant commensal bacteria as vaccine carriers, such as *Streptococcus* spp. and *Lactococcus* spp.

However, a potential problem with such recombinant organisms is that they may colonise the mucosal surfaces thereby generating a long term exposure to the target antigens expressed and released by these recombinant micro-organisms. Such long term exposure can cause immune tolerance. In addition, the mere fact alone that such organisms are genetically modified and contain recombinant nucleic acid is meeting considerable opposition from the (lay) public as a whole, stemming from a low level of general acceptance for products containing recombinant DNA or RNA. Similar objections exist against the use of (even attenuated) strains of a pathogenic nature or against proteins or parts of proteins derived from pathogenic strains. However, as explained above, present techniques of heterologous surface display of proteins in general entail the use of anchoring or targeting proteins that are specific and selective for a limited set of micro-organisms which in general are of recombinant or pathogenic nature, thereby greatly restricting-their potential applications.

The invention provides substances and methods to anchor or attach said substances to a cell-wall or cell-wall component of a wide range of micro-organisms. A preferred embodiment of the invention provides substances and methods to attach said substances to non-recombinant micro-organisms. Said substances provided by the invention are not limited to (chimeric) proteins alone, but can be fully or only partly of a peptide nature, whereby a peptide part is (covalently) joined to a non-peptide moiety. The invention provides a proteinaceous substance comprising at least one stretch of amino acids derived from a first micro-organism which substance is capable of attaching to a cell-wall of a second micro-organism. Said substance according to the invention is for example produced by a first micro-organism (for example a micro-organism from which the knowledge about the sequence of said stretch of amino acids originates, but another (recombinant) micro-organism can produce said substance as well). After its production said substance is harvested, optionally stored for future use, and then brought in contact with said second micro-organism, where it attaches to its cell-wall. Alternatively, said substance is produced synthetically, by using established peptide synthesis technology. A preferred embodiment of the invention provides a substance wherein said second micro-organism is a non-recombinant micro-organism. With a substance provided by the invention it is now possible to attach or anchor for a example a heterologous or chimeric protein produced by a recombinant micro-organism to an innocuous non-recombinant micro-organism.

Figure 11:
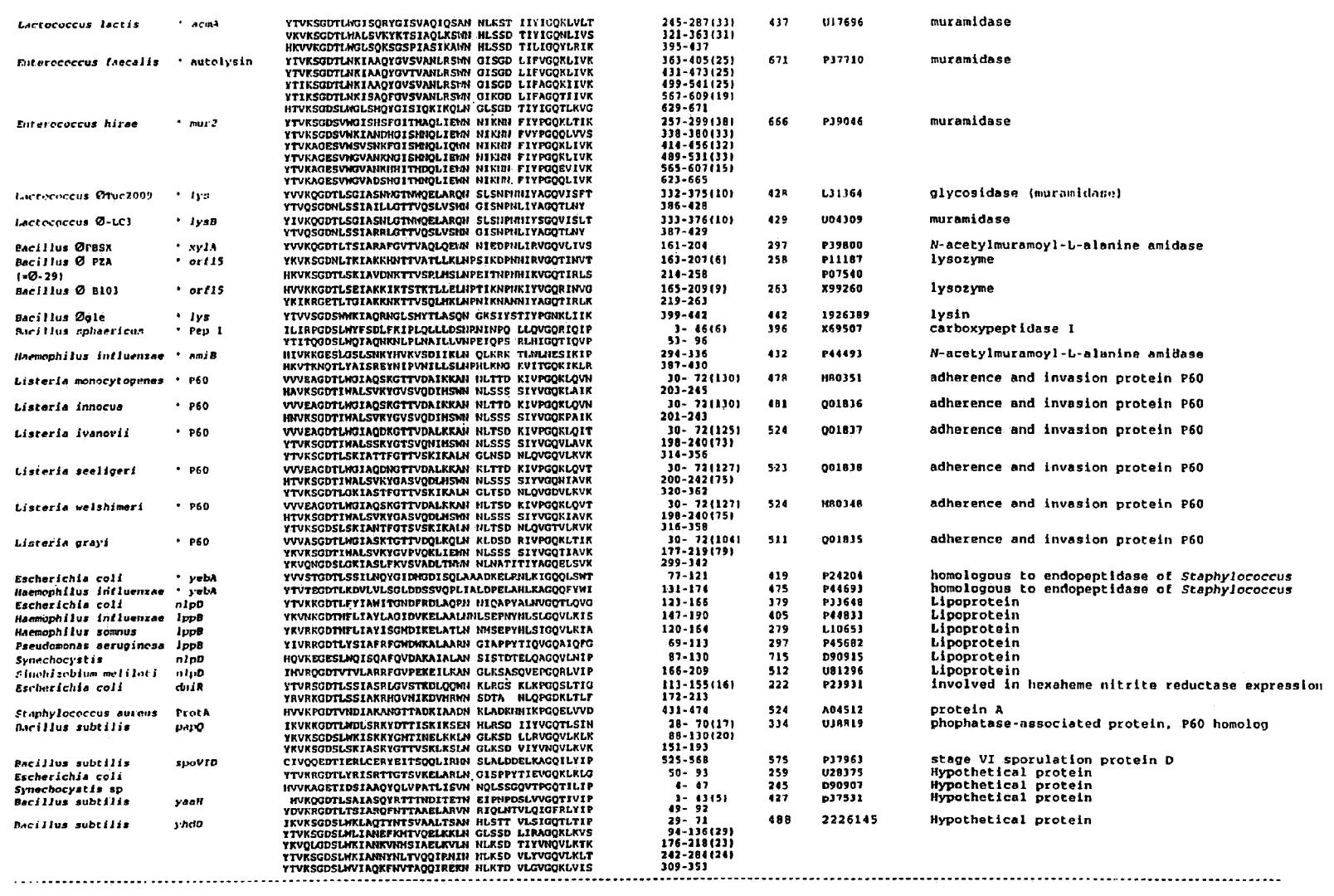

A preferred embodiment of the invention provides a proteinaceous substance wherein said stretch of amino acids has a sequence corresponding to a consensus sequence listed in FIG. 10 (SEQ ID NOS. 17), or wherein said stretch of amino acids (herein also called attaching peptide) has a sequence corresponding to a sequence selected from those listed in FIG. 11 (SEQ ID NOS. 20–110), or a homologous sequence derived from another species. The sequences listed in FIG. 11 (SEQ ID NOS. 20–110), and sequences homologuous thereto, are found in a variety of species, both micro-organisms and higher organisms, an example of such a higher organism is *C. elegans*. Preferably, the attaching peptide is derived from any one of the proteins listed in FIG. 11 (SEQ ID NOS. 20–110), more preferably said attaching peptide comprises an amino acid sequence as shown in FIG. 10 (SEQ ID NOS. 14–17), or a sequence derived thereof. For example, the invention provides a proteinaceous substance wherein said attaching peptide is derived from the major peptidoglycan hydrolase of *Lactococcus lactis*. (SEQ ID NOS. 14–16 and 20–22).

Yet another preferred embodiment of, the invention provides a proteinaceous substance wherein said second micro-organism is selected from any of the group of Gram-positive bacteria and Gram-negative bacteria. Examples are micro-organisms, such as *Bacillus subtilis* (SEQ ID NOS. 75–78, 81–87, 104, 107, 109–110); *Clostridium beij erinckii, Lactobacillus plantarum, Lb. buchneri, Listeria inocua, Streptococcus thermophilus, Enterococcus faecalis* (SEQ ID NOS. 23–27), *E. coli* (SEQ ID NOS. 64, 66, 72–73, 79, 106), and others.

The invention provides a proteinaceous substance which is additionally comprising a reactive group. For example, the invention provides a proteinaceous substance comprising a reactive group such as an antigenic determinant, heterologous enzyme, (single-chain) antibody or fragment thereof, polyhistidyl tag, fluorescing protein, luciferase, binding protein or peptide, or another substance such as an antibiotic, hormone, non-peptide antigenic determinant, carbohydrate, fatty acid, aromatic substance and reporter molecule, and an anchoring or targeting protein or part thereof (herein also called attaching peptide) useful in heterologous surface display which is both broadly reactive with cell wall components of a broad range of micro-organisms.

For example, the invention provides a substance wherein said reactive group is a non-protein moiety, for example is selected from the group of antibiotics, hormones, aromatic substances and reporter molecules. Said substance is constructed by binding for example an antibiotic, such as penicillin or tetracycline, but various other antibiotics can be used, or a hormone, such as a steroid hormone, or any other compound to an attaching peptide provided by the invention. Such binding can be achieved by various techniques known in the art, and thereby can label or "flag" the attaching peptide. A preferred example is the binding of an attaching peptide to a reporter molecule such as FITC, or HRPO, whereby tools are generated that can be used in diagnostic assay whereby micro-organisms having peptidoglycan are detected. Similarly, an attaching peptide with an antibiotic bound thereto can be used in vivo by for example parenteral administration into the bloodstream of humans or animals or in vitro to bind to such micro-organisms having peptidoglycan, thereby increasing the concentration of antibiotic around said organism, which then gets killed by the antibiotic action.

The invention provides a substance wherein said reactive group is a protein moiety, for example selected from the group of antigenic determinants, enzymes, (single-chain) antibodies or fragments thereof, polyhistidyl tags, fluorescing proteins, binding proteins or peptides. For example, the invention provides a protein, which comprises as reactive group a protein or (poly)peptide. Also, the invention provides a nucleic acid molecule encoding a protein provided by the invention. Such a nucleic acid molecule (being single- or double stranded DNA, RNA or DNA/RNA) at least comprises nucleic acid sequences specifically encoding a attaching peptide as well as nucleic acid sequences specifically encoding the reactive group polypeptide, but can additionally also comprise other nucleic acid sequences, which for example encode a signal peptide, or comprise for example promoter and/or regulatory nucleic acid sequences. The invention also provides a vector comprising a nucleic acid molecule encoding a protein provided by the invention.

The invention provides a proteinaceous substance comprising a reactive group joined with or bound to at least one attaching peptide which comprises a stretch of amino acids corresponding to the consensus amino acid sequence listed in FIG. 10, said substance capable of attaching or anchoring or binding to a cell wall component of a micro-organism.

Corresponding to is defined as having an amino acid sequence homologous to the consensus amino acid sequence listed in FIG. 10, or having an amino acid sequence derived of the sequence listed in FIG. 10 which derived sequence comprises a functionally equivalent stretch of amino acids.

Preferably, the attaching peptide is derived from any one of the proteins listed in FIG. 11, or a protein having a repeat sequence related or homologous to the sequence listed in FIG. 10, more preferably said attaching peptide comprises an amino acid sequence as shown in FIG. 10, or a sequence derived thereof. Homology between the various amino acid sequences of related attaching peptides provided by the invention can for instance be determined by performing a homology search between amino acid sequences, such as for example can be found in a protein database, such as the SWISSPROT, PIR and Genbank databases, using a computer programme, such as the BLAST programme, that can determine homology between amino acid sequences. For example, the invention provides a proteinaceous substance wherein said attaching peptide is derived from the major peptidoglycan hydrolase of *Lactococcus lactis*. The invention provides a proteinaceous substance comprising a reactive compound wherein at least two stretches of amino acids, corresponding to an attaching peptide sequence, are located adjacent to each other, possibly separated by one or more amino acid residues. Said stretches or repeats can be separated by a short distance, for example 3–6 to 10–15 amino acids apart, or by a medium distance 15–100 amino acids apart, or by longer distances (>100 amino acid residues apart). Examples of such distances can be found in FIG. 11, but longer distances are also possible. The distances between said stretches or repeats can also be used for an (additional) reactive group, whereby a reactive group is inserted between repeats, thereby allowing an even better anchoring to a cell wall component. A preferred embodiment provided by the invention is a proteinaceous substance comprising a reactive group and at least one attaching peptide which comprises a stretch of amino acids having a sequence corresponding to the consensus amino acid sequence listed in FIG. 10, wherein said substance is capable of attaching to a cell wall component of a micro-organism, such as can be found among from any of the group of yeast, moulds, Gram-positive bacteria and Gram-negative bacteria. Examples are micro-organisms, such as *Bacillus subtilis, Clostridium beijerinckii, Lactobacillus plantarum, Lb. buchneri, Listeria inocua, Streptococcus thermophilus, Enterococcus faecalis, E. coli*, and others. A preferred embodiment provided by the invention is a proteinaceous substance which is capable of attaching to a cell wall component of a conventional (non-recombinant) micro-organism. In this embodiment, the invention provides for example non-recombinant organisms which displaying heterologous proteins, these may colonise the mucosal surfaces without causing problems such as immune tolerance, since they do not generate a long term exposure to the target antigens expressed. In addition, the mere fact alone that such organisms provided by the invention are not genetically modified and do not contain recombinant nucleic acid will alleviate the opposition from the (lay) public as a whole against recombinant micro-organisms, which is stemming from a low level of general acceptance for products containing recombinant DNA or RNA. Similar objections that exist against the use of (even attenuated) strains of a pathogenic nature or against proteins or parts of proteins derived from pathogenic strains are now also overcome by the invention, in that is now possible to attach a proteinaceous substance to a non-recombinant, non-pathogenic micro-organism, such as *L. lactis* which is generally considered as safe. The invention provides a proteinaceous substance comprising a reactive group such as an antigenic determinant, (heterologous) enzyme, (single-chain) antibody or fragment thereof, polyhistidyl tag, fluorescing protein, luciferase, binding protein or peptide, or another compound such as an antibiotic, hormone, non-peptide antigenic determinant, carbohydrate, fatty acid, aromatic compound and reporter molecule, and an anchoring or targeting protein or part thereof (herein also called attaching peptide) useful in heterologous surface display which is both broadly reactive with cell wall components of a broad range of micro-organisms. Said attaching peptide is preferably derived from a micro-organism which is generally recognised as safe (G.R.A.S.), thereby greatly enhancing the potential of applications of the heterologous surface display technique. *Lactococcus lactis* is a non-pathogenic, non-invasive, and non-colonising Gram-positive bacterium which is not adapted for growth in body or even the gut; it does not belong to the commensal species of lactic acid bacteria. *L. lactis* has a history of safe use of several thousand years. The major cell wall hydrolase AcmA of the Gram-positive bacterium *Lactococcus lactis* subsp. *cremoris* MG1363 is an N-acetylmuramidase which is required for cell separation and is responsible for cell lysis during stationary phase. The protein consists of three separate domains (FIG. 9, Buist et al., J. Bacteriol. (1995) 177: 1554–1563) of which the first 57 amino acids of the N-terminal domain encompasses the signal peptide needed for secretion. This domain is followed by the active site domain running from the Ala at position 58 to Ser-218. The active site domain was overproduced in and purified from *Escherichia coli* as a thioredoxin fusion protein. The AcmA part was released by proteolytic cleavage with enterokinase and shown to be active in vitro. Three homologous repeated regions (or stretches of amino acids) of 35–55, more often 40–50 amino acid residues are present in the C-terminus of for example AcmA which are separated by non-homologous sequences (FIG. 10). The repeat sequences of AcmA (cA) can be deleted and additional repeat sequences could be added without impairing cell wall hydrolysing activity in vitro. The AcmA deletion derivatives lacking one or two repeat sequences and the protein containing at least one additional repeat were able to bind to lactococcal cells when added from the outside. The derivative lacking all three repeats did not bind to the cells nor did the purified active site domain. The invention provides an attaching peptide that comprise at least one repeat sequence as shown in FIG. 10 or a sequence that is similar to the sequence of FIG. 10, similar being defined as comprising at least a part of a consensus sequence as shown in FIG. 11. Also, attaching peptides are provided by the invention which are comprising amino acid sequences that are derived from a sequence as shown in FIG. 11. Derived herein meaning among others by comparison with heterologous sequences whereby a consensus sequence is obtained, or derived via conventional amino acid substitutions whereby amino acids are being substituted by like amino acids, or derived via substitutions whereby functional amino acids are being replaced by functionally alike or better amino acids identified by methods such as PEPSCAN techniques or replacement mapping. The invention provides a proteinaceous substance comprising a reactive group and at least one attaching peptide which comprises a stretch of amino acids having a sequence corresponding to at least a part of the consensus amino acid sequence provided in FIG. 10. Repeats similar to those in AcmA were for example shown to be present in various cell wall hydrolases and other (secreted) proteins of Gram-positive and Gram-negative bacteria and other micro-organisms and constitute a general cell wall binding domain in these proteins. An attaching peptide comprising at least one AcmA repeat or an amino acid sequence similar to the AcmA repeat provided by the invention represents a general and broadly reactive tool to bind or attach reactive groups such as antigenic determinants, enzymes, antibodies, proteins or peptides to cell walls of micro-organisms. Said repeat comprises a peptide composed of a stretch of amino acids having a sequence corresponding to at least a part of the consensus amino acid sequence provided in FIG. 10. Furthermore, we also demonstrated that an attaching peptide provided by the invention bound or attached to cells of other, e.g. non-recombinant micro-organisms, such as *Bacillus subtilis, Clostridium beijerinckii, Lactobacillus plantarum, Lb. buchneri, Listeria inocua, Streptococcus thermophilus, Enterococcus faecalis, E. coli*, and others. Binding of the attaching peptide and reactive group joined therewith, as provided by the invention is stable at pH values ranging from 2–10. Moreover, the attaching peptide provided by the invention is, when attached to the cell wall, protected against proteolytic degradation. One embodiment of the invention is a protein wherein the attaching peptide is derived from any of the proteins listed in FIG. 11. An example of such an attaching peptide is provided in the experimental part of this description wherein an attaching peptide having a sequence as shown in FIG. 10, or a sequence similar thereto, is used. Furthermore, the invention provides a protein, which comprises as reactive group a protein or (poly)peptide. Also, the invention provides a nucleic acid molecule encoding a protein provided by the invention. Such a nucleic acid molecule (being single- or double stranded DNA, RNA or DNA/RNA) at least comprises nucleic acid sequences specifically encoding a attaching peptide as well as nucleic acid sequences specifically encoding the reactive group polypeptide, but can additionally also comprise other nucleic acid sequences, which for example encode a signal peptide, or comprise for example promoter and/or regulatory nucleic-acid sequences. The invention also provides a vector comprising a nucleic acid molecule encoding a protein provided by the invention. Such a vector can for example be a plasmid, phage, or virus, and can now be constructed using a nucleic acid provided by the invention and routine skills of the art. Examples of such a vector can be found in the experimental part of the description, other examples can e.g. be a baculovirus vector, or comparable vector viruses through which a protein provided by the invention can be expressed or produced in (insect) cells. The invention also provides a host cell or expression system comprising a nucleic acid molecule according to the invention or a vector according to the invention. Such a host cell expressing a protein is in it self provided by the invention as a micro-organism to which a protein provided by the invention is attached. Such a host cell or expression system can for example be a Gram-positive- or Gram-negative bacterium, or a yeast cell or insect cell or plant- or mammalian cell, or even a cell-free expression system such as a reticulocyte lysate, and can now be constructed or obtained using a nucleic acid or vector provided by the invention and routine skills of the art. Examples of such a host cell or expression system can be found in the experimental part of the description, other examples can be obtained using a nucleic acid or vector provided by the invention and routine skills of the art.

The invention provides a method for attaching a substance to the cell wall of a micro-organism comprising the use of an attaching peptide which comprises a stretch of amino acids having a sequence corresponding to at least a part of the consensus amino acid sequence provided in FIG. 10. An example of the method provided by the invention is anchoring of recombinant poly(peptides), being (chimeric) proteins fused to the cell wall anchoring repeats of AcmA of *Lactococcus lactis* MG1363, to the cell wall of (Gram-positive) bacteria. The recombinant proteins are obtained by the expression of DNA sequences encoding these recombinant (poly)peptides in a suitable production strain (e.g. *E. coli* or *L. lactis*) and subsequent purification of the expression products. The recombinant proteins are than mixed, either in vitro or in vivo, with a non-recombinant target bacterium to obtain binding to the cell wall. Another example of the method provided by the invention is anchoring of recombinant poly(peptides), being (chimeric) proteins fused to the cell wall anchoring repeats of AcmA of *Lactococcus lactis*, to the cell wall of said recombinant *Lactococcus lactis* which produces the protein itself. In a preferred embodiment of the method provided by the invention the binding of (purified) proteins to bacterial cells upon addition from the outside, the method is an excellent tool to anchor recombinant proteins or other substances to non-recombinant bacterial cells.

A preferred method according to the invention comprises the use of an attaching peptide which is derived from the major peptidoglycan hydrolase of *Lactococcus lactis*. Another method according to the invention is provided wherein said substance is a (poly)peptide or a protein, for example being part of a protein provided by the invention. Post-translational modifications occurring to such a (poly) peptide or protein are inherent to the host cell or expression system used, a post-translationally modified protein as provided by the invention is therefore also provided. However, yet another method according to the invention is provided wherein said compound is selected from the group composed of antibiotics, hormones, antigenic determinants, carbohydrate chains, fatty acids, aromatic compounds and reporter molecules. Said substance is constructed by binding for example an antibiotic, such as penicillin or tetracycline, but various other antibiotics can be used, or a hormone, such as a steroid hormone, or any other compound to an attaching peptide provided by the invention. Such binding can be achieved by various techniques known in the art, and thereby can label or "flag" the attaching peptide. A preferred example is the binding of an attaching peptide to a reporter molecule such as FITC, or HRPO, whereby tools are generated that can be used in diagnostic assay whereby micro-organisms having peptidoglycan are detected. Similarly, an attaching peptide with an antibiotic bound thereto can be used in vivo by for example parenteral administration into the bloodstream of humans or animals or in vitro to bind to such micro-organisms having peptidoglycan, thereby increasing the concentration of antibiotic around said organism, which than can get killed by the antibiotic action. Said micro-organism is preferably selected from any of the group of yeast, moulds, Gram-positive bacteria and Gram-negative bacteria. For example, the experimental part of this description describes mixing of β-lactamase::cA fusion protein with lactococcal cells which resulted in binding to the cells whereas this was not the case when mature β-lactamase not joined with an attachement protein was added. Also, fusion of β-lactamase of *E. coli* and α-amylase of *Bacillus licheniformis* to the attaching peptide provided by the invention and subsequent production of these fusion proteins resulted in active, secreted proteins which were located (attached) in *L. lactis* cell walls. Binding of AcmA and the β-lactamase::cA fusion protein was also demonstrated to isolated lactococcal cell walls and SDS-washed cell walls (the major part of this fraction is peptidoglycan).

Anchoring of recombinant proteins to non-recombinant micro-organisms such as lactococci (or other bacteria) or fungi, is especially attractive if the use of recombinant bacteria is not desired, e.g. in food processes or as pharmaceuticals for medical use such as in vaccines or in antibacterial therapy. The invention provides for example vaccine delivery or immunisation via micro-organisms provided by the invention which are labelled with distinct antigenic determinants, which may be directed against a wide variety of diseases. A protective immune response can for example be elicited by oral delivery of a bacterial vaccine provided by the invention wherein tetanus toxin fragment C is attached via a protein provided by the invention to a non-recombinant *Lactococcus lactis*. Such immunogens expressed by micro-organisms provided by the invention are presented in particulate form to the antigen-presenting cells (for example M-cells) of the immune system and are therefore less likely to induce tolerance than soluble antigens. In addition, the existence of a common mucosal immune system permits immunisation on one specific mucosal surface to induce secretion of antigen-specific IgA, and other specific immune responses at distant mucosal sites. The invention solves the drawback of earlier bacterial vaccines whereby the potential to flourish on mucosal surfaces of the (attenuated or recombinant) bacterial strain used can cause problems such as inflammation and disease in itself, potentially leading to fever and bacteraemia, or to the induction of immune tolerance. Also, the invention avoids the potential risks that are involved when using recombinant DNA containing bacterial vectors for vaccination. In yet another possible vaccine and vaccine use provided by the invention, certain (killed) micro-organisms with adjuvant properties (such as the mycobacteria used in BCG) are labelled or loaded with a protein or substance composed of an antigenic determinant and an attaching peptide. These micro-organisms than function as adjuvant, thereby greatly enhancing the immune response directed against the specific antigenic determinant. Yet another use provided by the invention comprises anchoring proteins from the outside to a micro-organism which provides a means to present proteins or peptides which normally can not be overexpressed (and/or secreted) by said micro-organism. For example, the subunit B of cholera toxin (CTB) can be overproduced in *E. coli* but expression in *L. lactis* has been unsuccessful until now. The adjuvant activity of CTB in experimental recombinant vaccines is well documented and the ability of CTB or part thereof to bind to GM1 ganglioside on eucaryotic cell surfaces is of interest with respect to the use of *L. lactis* (or other Gram-positives) in vaccines which specifically require targeting to mucosal surfaces. Yet another medical use provided by the invention is the addition of (purified) antigen::cA fusion proteins in vivo by parenteral administration into the bloodstream of humans or animals to combat bacterial infections. In this case the antigen::cA fusion protein is used as a "flag" for the immune system. The antigenic determinant of a protein provided by the invention being a subunit of a vaccine regularly used for the immunisation of humans (preferably children) or animals, e.g. a subunit of the Rubella, Pertusis, Poliomyelitis, tetanus or measles vaccine. After delivery in the bloodstream, the "flag" will bind through the AcmA repeats to the pathogenic bacterium present in the blood. A "flag" protein provided by the invention will then activate a memory response, i.e. the response to the antigenic determinant present in the protein. The antibodies thus produced recognise the "flag"—labelled bacteria, which will then be neutralised by the immune system. In this way the protein is used to stimulate a pre-existing (memory) immune response, non-related to the bacterial infection, to clear bacterial infections from the system. Yet another use (which alternatively may be considered medical use or food use) provided by the invention is the use wherein a protein provided by the invention has the ability to bind to cells, such as mucosal cells, e.g. of the gut. The reactive group of such a protein is in such a case for example partly or wholly derived from a fimbriae protein or another gut attachment protein, as for example present in various *E. coli* strains. Micro-organisms to which such a protein is attached will specifically home or bind to certain areas of the gut, a property which for example is beneficial for certain bacterial strains (i.e. lactococcal or lactobacillar strains) used as a probiotic. In another food or use of food provided by the invention, the protein or substance provided by the invention is a composed of a food additive (such as an enzyme or flavour compound) which affects quality, flavour, shelf-life, food value or texture, joined with an attaching peptide, and subsequently attached or anchored to a micro-organism which is than mixed with the foodstuff. The anchoring of such proteins to a bacterial carrier offers the additional advantage that the additive can be targeted to a solid (bacteria-containing) matrix (e.g. curd) in a process for the preparation of food, e.g. cheese or tofu. Yet another use of a proteinaceous substance or micro-organism provided by the invention is the use of bacterial surface display in generating whole-cell bioadsorbents or biofilters for environmental purposes, microbiocatalysts, and diagnostic tools The invention is further explained in the experimental part which can not be seen as limiting the invention.

EXPERIMENTAL PART

Introduction

The major autolysin AcmA of *Lactococcus lactis* subsp. *cremoris* MG1363 is an N-acetylmuramidase which is required for cell separation and is responsible for cell lysis during stationary phase (5, 6). The 40.3-kDa secreted mature protein produces a number of activity bands in a zymogram of the supernatant of a lactococcal culture. Bands as small as that corresponding to a protein of 29 kDa were detected. As no clearing bands are produced by an *L. lactis* acmA deletion mutant, all bands represent products of AcmA (6). From experimental data and homology studies we inferred that AcmA likely consists of three domains: a signal sequence followed by an active site domain and a C-terminal region containing three highly homologous repeats of approximately 45 amino acids which are involved in cell wall binding. As the smallest active protein is 29 kDa, it was suggested that the protein undergoes proteolytic breakdown in the C-terminal portion (5, 6).

Cell wall hydrolases of various bacteria and bacteriophages contain repeats similar to those present in AcmA (4, 9, 10, 17). Partially purified muramidase-2 of *Enterococcus hirae*, a protein similar to AcmA, containing 6 similar repeats, binds to peptidoglycan fragments of the strain (11). The p60 protein of *Listeria monocytogenes* contains two such repeats and was shown to be associated with the cell surface (24). However, which parts of these enzymes contained the binding capacity was not assessed in any of these studies.

Nearly all cell wall hydrolases examined so far seem to consist of a catalytic domain and usually, although not always, a domain containing a number of specific amino acid repeats. In several studies it has been shown that only a part of some of the cell wall hydrolases is required for enzymatic activity (13, 14, 17, 19, 22, 34). Rashid et al. reported the cloning of the gene encoding a 90-kDa glucosamimidase of *Bacillus subtilis* of which the C-terminus shows significant similarity with the glucosamimidase domain of the *S. aureus* autolysin (23). The protein contains two repeated sequences in its N-terminus and two different repeats in the middle domain. A deletion derivative lacking the C-terminal 187 amino acids remained tightly bound to the cell walls, but no catalytic activity was observed when expressed in *B. subtilis*. By making deletions from the N-terminus it was shown that nearly two-thirds of the protein could be removed without complete loss of cell wall-hydrolyzing activity in *E. coli*, although loss of more than one repeat drastically reduced lytic activity.

The N-terminal domain of the major autolysin LytA of *Streptococcus pneumonia* provides the N-acetylmuramyl-L-alanine amidase catalytic function, whereas the C-terminal domain, which contains six repeated sequences, determines the specificity of binding to the cell wall (for review: see reference 18). The protein lacks a signal sequence and requires choline-containing teichoic acids to fully degrade pneumococcal cell walls. Furthermore, it was shown that at least four of the six repeats were needed for efficient recognition of the choline residues of pneumococcal cell walls and the retention of appreciable hydrolytic activity (7).

LytA, pneumococcal phage lysins as well as clostridial and lactococcal cell wall hydrolases have been used for the construction of active proteins such that the activity domain and cell wall recognition domains were exchanged. The N-terminal half of the lactococcal phage enzyme was fused to the C-terminal domain of LytA (28). The chimeric enzyme exhibited a glycosidase activity capable of hydrolyzing choline-containing cell walls of *S. pneumonia*. This result showed that the lactococcal phage lysin consisted of at least two domains with a glucosidase activity contained in its N-terminus and two repeats similar to those in AcmA in the C-terminus (6). A tripartite pneumococcal peptidoglycan hydrolase has been constructed by fusing the N-terminal catalytic domain of the phage CPL1 lysozyme to HBL3, a protein with an amidase activity and a choline-binding domain (27). The three domains acquired the proper conformation as the fusion protein behaved as an amidase, a lysozyme and as a choline-dependent enzyme.

Also from nature an enzyme is known having two separate functional activity domains: the autolysin gene from *Staphylococcus aureus* encodes a protein that contains an amidase and an endo-β-N-acetylglucosaminidase domain separated by three highly similar repeats (20). This protein is processed posttranslationally into the two constituting activity domains.

The aim of the present study was to investigate the modular structure of AcmA. This was done by consecutively deleting the C-terminal repeats and by fusing the repeats to heterologous proteins. On the basis of cell fractionation and binding studies involving whole cells, it is concluded that the C-terminal repeats in AcmA bind the autolytic enzyme to the cell wall of *L. lactis*.

MATERIALS AND METHODS

Bacterial strains, plasmids, and growth conditions. The strains and plasmids used in this study are listed in Table 1. *Lactococcus lactis* was grown at 30° C. in two-fold diluted M17 broth (Difco Laboratories, Detroit, Mich.) containing 0.5% glucose and 0.95% β-glycerophosphate (Sigma Chemical Co., St. Louis, Mo.) as standing cultures (½M17). Agar plates of the same medium contained 1.5% agar. Five µg/ml of erythromycin (Boehringer GmbH, Mannheim, Germany) was added when needed. *Escherichia coli* was grown at 37° C. with vigorous agitation in TY medium (Difco), or on TY medium solidified with 1.5% agar. When required, the media contained 100 µg of ampicillin (Sigma), 100 µg erythromycin or 50 µg kanamycin (both from Boehringer) per ml. Isopropyl-β-D-thiogalactopyranoside (IPTG) and 5-bromo-4-chloro-3-indolyl-β-D-galactopyranoside (X-gal) (both from Sigma) were used at concentrations of 1 mM and 0.002%, respectively.

General DNA Techniques and Transformation.

Molecular cloning techniques were performed essentially as described by Sambrook et al. (25). Restriction enzymes, Klenow enzyme and T4 DNA ligase were obtained from Boehringer and were used according to the instructions of the supplier. Deoxynucleotides were obtained from Pharmacia (Pharmacia Biotech, Uppsala, Sweden). All chemicals used were of analytical grade and were from Merck (Darmstadt, Germany) or BDH (Poole, United Kingdom). Electrotransformation of *E. coli* and *L. lactis* was performed by using a gene pulser (Bio-Rad Laboratories, Richmond, Calif.), as described by Zabarovsky and Winberg (37) and Leenhouts and Venema (16), respectively. Plasmid DNA was isolated using the QIAGEN plasmid DNA isolation kit (QIAGEN GmbH, Hilden, Germany) or by CsCl-ethidium-bromide density gradient centrifugation and DNA fragments were isolated from agarose gels using the QIAGEN gel extraction kit and protocols from QIAGEN.

Primer Synthesis, PCR and DNA Sequencing.

Synthetic oligo deoxyribonucleotides were synthesized with an Applied Biosystems 392 DNA/RNA synthesizer (Applied Biosystems Inc., Foster City, Calif.). The sequences of the oligonucleotides used are listed in Table 2.

Polymerase chain reactions (PCR) were performed in a Bio-Med thermocycler 60 (Bio-Med GmbH, Theres, Germany) using super Taq DNA polymerase and the instructions of the manufacturer (HT Biotechnology Ltd., Cambridge, United Kingdom). PCR fragments were purified using the nucleotide removal kit and protocol of QIAGEN.

Nucleotide sequences of double-stranded plasmid templates were determined using the dideoxy chain termination method (26) with the T7 sequencing kit and protocol (Pharmacia) or the automated fluorescent DNA sequencer 725 of Vistra Systems (Amersham Life Science Inc., Buckinghamshire, United Kingdom).

Nucleotide and amino acid sequences were analyzed with the PC/GENE sequence analysis program (version 6.8. IntelliGenetics, Inc., Geneva, Switzerland). Protein homology searches in the SWISSPROT, PIR, and Genbank (release Sep. 23, 1996) databases were carried out with the BLAST program (1).

Construction of Acmh Derivatives.

A stop codon and EcoRI restriction enzyme site were introduced in acmA at the end of nucleotide sequences encoding the repeats and at the end of the sequence specifying the 35 active site domain by PCR using the primers. REPDEL-1 (SEQ ID NO. 1), REPDEL-2 (SEQ ID NO. 2), and REPDEL-3 (SEQ ID NO. 3) and plasmid pAL01 as a template. Primer ALA-4 (SEQ ID NO. 4), annealing within the sequence encoding the signal peptide of AcmA, was used in all cases as the upstream primer. All three PCR products were digested with SacI and EcoRI and cloned into 5 the corresponding sites of pBluescript SK+ leading to pDEL1, pDEL2 and pDEL3. Subsequently; the 1,187-bp PflmI-EcoRI fragment of pGKAL1 (5) was replaced by the 513, 282. and 76—by PflmI-EcoRI fragments of the inserts of pDEL1, 2 and 3, respectively. The proper plasmids specifying proteins containing one, two or all three repeats (pGKAL5, 4, and ~3, respectively) were obtained in *L. lactis* MG1363acmAΔ1. pGKAL1 was cut with SpeI. The sticky ends were flushed with Klenow enzyme and self-ligation introduced a UAG stop codon after the Ser 339 codon of acmA. The resulting plamid was named pGKAL6.

A DNA fragment encoding half of the first repeat until the SpeI site in the middle of the second repeat was synthesized by PCR using the primers REP-4 A (SEQ ID NO. 5) and B (SEQ ID NO. 6). The NheI and SpeI sites at the ends of the 250-bp PCR product were cut and the fragment was cloned into the unique SpeI site of pGKAL1 resulting in plasmid pGKAL7.

Overexpression and Isolation of the AcmA Active Site Domain.

A DNA fragment encoding the active site domain of AcmA was obtained using the primers ACMHIS (SEQ ID NO. 7) and REPDEL-3 with plasmid pAL01 as a template. The 504-bp PCR fragment was digested with BglII and EcoRI and subcloned into the BamHI and BcoRI sites of pET32A (Novagen R&D systems Europe Ltd, Abingdon, United Kingdom). The proper construct, pETAcmA, was obtained in *E. coli* BL21(DE3) (30). Expression of the thioredoxin/AcmA fusion protein was induced in this strain by adding IPTG (to 1 mM final concentration) at an OD600 of 0.7. Four hours after induction the cells from 1 ml of culture were collected by centrifugation and the fusion protein was purified over a Talon™ metal affinity resin (Clontech Laboratories Inc., Palo Alto, Calif.) using 8 M ureum-elution buffer and the protocol of the supplier. The eluate (200 µl) was dialyzed against a solution containing 50 mM NaCl and 20 mM Tris (pH 7) after which $CaCl_2$ was added to a final concentration of 2 mM. One unit of enterokinase (Novagen) was added and the mixture was incubated at room temperature for 20 h. The protein mixture was dialyzed against several changes of demineralized water before SDS-PAGE analysis and cell binding studies.

Construction of β-lactamase and α-amylase Fusions to the AcmA Repeat Domain.

For the introduction of a unique NdeI site at the position of the stop codon of the *E. coli* TEM-p-lactamase, the oligonucleotides BETA-1 (SEQ ID NO. 8) and BETA-2 (SEQ ID NO. 9) were used in a PCR with plasmid pGBL1 (21) as a template. The 403-bp PCR fragment was cut with NdeI and PstI and cloned as a 311-bp fragment into the same sites of pUK21. The resulting plasmid, pUKblac, was digested with NdeI, treated with Klenow enzyme and subsequently digested with XbaI. The β-lactamase encoding fragment was ligated to an 1,104-bp PvuII-XbaI DNA fragment from pAL01 containing the acmA part encoding the repeat region of AcmA. The resulting plasmid, pUKbla-crep, was digested with PstI and DraI and the 1349-bp fragment was inserted into the PstI-SnaBI sites of pGBL1, leading to plasmid pGBLR. After digestion of pGAL9 (21) with ClaI and HindIII the 1,049-bp fragment encompassing the 3'-end of the *Bacillus licheniformis* α-amylase gene was subcloned into corresponding sites of pUK21. According to the paper of Perez Martinez et al. (21), this fragment should be 1,402-bp, but after restriction enzyme analysis it turned out to be approximately 350—by smaller. The resulting plasmid was called pUKAL1. A unique EcoRV restriction enzyme site was introduced by PCR at the position of the stop codon of the *B. licheniformis* α-amylase gene using the oligonucleotides ALFA-A (SEQ ID NO. 10) and ALFA-B (SEQ ID NO. 11) with plasmid pGAL9 as a template. After restriction of the 514-bp PCR fragment with SalI and BcoRV the 440-bp fragment was cloned into the same sites of pUKAL1 resulting in plasmid pUKAL2. The EcoRV and XbaI sites of this plasmid were used to clone the 1,104-by PvuII-XbaI fragment of pAL01 encoding the repeats of AcmA. The 1,915-bp ClaI-HindIII fragment of the resulting plasmid pUKALR was used to replace the corresponding 1,049-bp fragment of pGAL9 (pGALR). All cloning steps described above were performed in *E. coli* NM522. The plasmids pGBL1, pGBLR, pGAL9 and pGALR were used to transform *L. lactis* MG1363 and MG1363acmAΔ1.

SDS-polyacrylamide Gel Electrophoresis (SDS-PAGE) and Detection of AcmA and α-amylase Activity.

Two ml of end exponential phase *L. lactis* cultures were subjected to centrifugation. 0.5 ml of the supernatant fractions were dialyzed against several changes of demineralized water, lyophilized, and dissolved in 0.25 ml of denaturation buffer (3). Cell pellets were washed with 2 ml of fresh ½M17 medium and resuspended in 1 ml of denaturation buffer. Cell extracts were prepared as described by van de Guchte et al. (32).

AcmA activity was detected by a zymogram staining technique using SDS-PAA (12.5% or 17.5%) gels containing 0.15% autoclaved, lyophilized *Micrococcus lysodeikticus* ATCC 4698 cells (Sigma) as described before (6). For the analysis of α-amylase activity 1% starch was included into 12.5% PAA gels. After electrophoresis proteins were renatured using the AcmA renaturation solution (3) and the gel was stained with an $I_2$/KI solution (at final concentrations of 12 and 18 mM, respectively) (33).

SDS-PAGE was carried out according to Laemmli (15) with the Protean II Minigel System (Bio-Rad) and gels were stained with Coomassie brilliant blue (Bio-Rad). The standard low range and prestained low and high range SDS-PAGE molecular weight markers of Bio-Rad were used as references.

Fractionation of mid- and end-exponential phase cultures of *L. lactis* was performed according to the protocol of Baankreis (2).

Binding of AcmA and its Derivatives to Lactococcal Cells.

The cells of 2 ml of exponential phase cultures of MG1363acmAΔ1 were gently resuspended in an equal volume of supernatant of similarly grown MG1363acmAΔ1 carrying either plasmid pGK13, pGKAL1, -3, -4, -5, -6 or -7 and incubated at 30° C. for 20 min. Subsequently, the mixtures were centrifuged. The cell pellets were washed with 2 ml of ½M17 and cell extracts were prepared in 1 ml of denaturation buffer as described above, while 0.4 ml of the supernatants were dialyzed against demineralized water, lyophilized and dissolved in 0.2 ml of denaturation buffer.

To analyze competitive binding between AcmA derivatives containing 1 or 2 repeats, equal volumes of the supernatants of MG1363acmAΔ1 containing pGKAL3 or pGKAL4 were mixed prior to incubation with the MG1363acmAΔ1 cells. The samples were treated for SDS-PAGE as described above.

Three 500 µl samples of a mid-exponential phase culture of MG1363acmAΔ1 were centrifuged. From one sample 50 µl of the supernatant were replaced by 50 µl of a solution containing the AcmA active site domain (see above). 100 µl of the supernatant of sample two were replaced by 50 µl demineralized water and 50 µl of the supernatant of a mid-exponential phase culture of MG1363acmAΔ1 (pGKAL4). Of the third sample 100 µl of the supernatant were replaced by 50 µl of the solution containing the AcmA active site domain and 50 µl of the supernatant of MG1363acmAΔ1 (pGKAL4). Subsequently the three samples were vortexed to resuspend the cells and incubated for 15 min at 30° C. After centrifugation cell and supernatant fractions were prepared in 500 µl of denaturation buffer for analysis of AcmA activity in SDS-(17.5%)PAGE as described above.

Binding of the β-lactamase/AcmA fusion protein was studied by growing MG1363acmAΔ1 containing pGK13, pGBL1 or pGBLR until mid-exponential phase. The cells of 1 ml of MG1363acmAΔ1(pGK13) culture were resuspended in an equal volume of supernatant of either of the other two cultures. The mixtures were prepared in duplo and one series was incubated at 30° C. for 5 min while the other was kept at that temperature for 15 min. Then, cell and supernatant fractions were treated as described for the AcmA binding studies, resuspended in denaturaion buffer in half of the original volume, and subjected to SDS-(12.5%)PAGE followed by Western blot analysis.

Western Blotting and Immunodetection.

Proteins were transferred from SDS-PAA gels to BA85 nitrocellulose membranes (Schleicher and Schuell, Dassel, Germany) as described before (31). α-amylase and β-lactamase antigen was detected with 2000-fold diluted rabbit polyclonal anti-ampicillinase antibodies (5 prime→+3 prime, Inc., Boulder, Co.), and alkaline phosphatase-conjugated goat anti-rabbit antibodies (Promega Corporation, Madison, Wis.) using the Western-Light Chemiluminescent detection system and protocol (TROPIX Inc., Bedford, Mass.).

Enzyme Assays and Optical Density Measurements.

AcmA activity was visualized on ½M17 agar plates containing 0.2% autoclaved lyophilized *M. lysodeikticus* cells as halo's around colonies after overnight growth at 30° C.

α-amylase activity was detected by spotting 10 µl of an overnight culture onto a ½M17 agar plate containing 1% of starch (Sigma). After 18 h of incubation at 30° C. halo's were visualized by staining with an iodine solution according to the protocol of Smith et al. (29). A similar method was used for the detection of β-lactamase activity (29).

X-prolyl dipeptidyl aminopeptidase (PepX) was measured using the chromogenic substrate Ala-Pro-p-nitroanilid (BACHEM Feinchemicalien AG, Bubendorf, Switserland). After 2 min of centrifugation in an eppendorf microcentrifuge 75 µl of a culture supernatant was added to 50 µl substrate (2 mM) and 75 µl Hepes buffer (pH 7). The mixture was pipetted into a microtiter plate well and colour development was monitored in a THERMOmax microtiter plate reader (Molecular Devices Corporation, Menlo Oaks, Calif.) at 405 nm during 20 minutes at 37° C. Optical densities were measured in a Novaspec II spectrophotometer (Pharmacia) at 600 nm.

RESULTS

Two of the Three Repeats in AcmA are Sufficient for Autolysis and Cell Separation.

Several mutant AcmA derivatives were constructed to investigate the function of the three repeats in the C-terminus of AcmA. A stop codon was introduced behind the codon for Thr-287 (pGKAL4) or Ser-363 (pGKAL3) (see FIG. 1). Plasmid pGKAL4-specified AcmA (A1) only contains the first (most N-terminal) of the three repeats, while pGKAL3 specifies an AcmA variant (A2) carrying the first two repeats. pGKAL5 specifies an AcmA derivative lacking repeats (A0) due to the introduction of a stop codon after Ser-218. AcmA specified by pGKAL6 contains one an a half repeat (A1.5) due to the presence of a stop codon behind the Ser-339 codon. From pGKAL7 an AcmA mutant (A4) is produced which carries an additional (fourth) repeat as the result of duplication of the polypeptide from Ser-263 to Thr-338. All proteins were expressed from the acmA promoter in the AcmA-negative strain L. lactis MG1363acmAΔ1. The various deletions of AcmA were examined with respect to the following properties: (I) their effect on halo formation on plates containing cell wall fragments of M. lysodeikticus, (II) chain length of the cells expressing the mutant AcmA's, and sedimentation of the cells in a standing culture, (III) their enzymatic activity, both in the cell and supernatant fraction and (IV) autolysis.

Halo formation. On a ½M17 plate containing cell wall fragments of M. lysodeikticus halo's were absent when MG1363acmAΔ1 carried pGK13 or pGKAL5. All other strains produced a clear halo that differed in size. The halo size was clearly correlated with the number of full length repeats present, although the addition of an extra repeat resulted in a reduced halo size (see Table 3). Apparently, for optimal cell wall lytic activity a full complement of repeats is required.

Cell separation and sedimentation. The deletion of one and a half, two and all three repeats had a clear effect on the chain length and on sedimentation of the cells after overnight growth (see Table 3). Thus, efficient cell separation requires the presence of at least two repeats in AcmA.

Enzyme activity. Cells and supernatants of overnight cultures of all strains were analyzed for AcmA activity by SDS-PAGE. In the cell fractions no activity was detected for A0, not even after one week of renaturation of the protein (Table 3). Of the other derivatives, two major activity bands were present in this fraction. In each case their positions in the gel corresponded to proteins with the calculated molecular weights of the unprocessed and the processed form. (Table 3 and not shown). As shown in FIG. 1, all AcmA derivatives were still active in the supernatant fractions. AcmA produced the characteristic breakdown pattern as determined before (FIG. 1, lanes 1 and 3; (6)). All AcmA derivatives except A0 and A1 also showed a distinct and highly reproducible degradation pattern. A4 showed 2 additional breakdown products after prolonged renaturation (results not shown). These data indicate that removal of the repeats does not destroy AcmA activity and suggests that one repeat is sufficient to keep the enzyme cell-associated.

Autolysis. To analyze the effect of the repeats on autolysis during stationery phase, overnight cultures of all strains were diluted hundred-fold and incubated at 30° C. for 6 days and the decrease of optical density ($OD_{600}$) was followed. All cultures exhibited similar growth rates, reached the same maximal optical densities and did not lyse during the exponential phase of growth. After approximately 60 h of incubation maximal reduction in $OD_{600}$ was reached in all cases. The results are presented in Table 3 and show that the reduction in $OD_{600}$ is correlated with the reduction of the number of AcmA repeats. To investigate whether the decrease in $OD_{600}$ really reflected autolysis, the activity of the intracellular enzyme PepX was measured. After 60 h of incubation, PepX activity in the culture medium was also maximal in all samples, decreasing in all cases upon further incubation. Hardly any PepX activity was detected in the supernatant of the acmAΔ1 mutant and in cultures producing A0, A1 or A1.5. In contrast, a considerable quantity of PepX had released into the supernatant of cultures producing A2 and A3. Thus two repeats in AcmA are sufficient for autolysis of L. lactis. A2 or A4 production led to reduced lysis of the producer cells. Taken together, these results indicate that the repeats in AcmA function in efficient autolysis and are required for cell separation.

The Active Site Domain of AcmA Resides in the N-Terminal Part.

Figure 2:
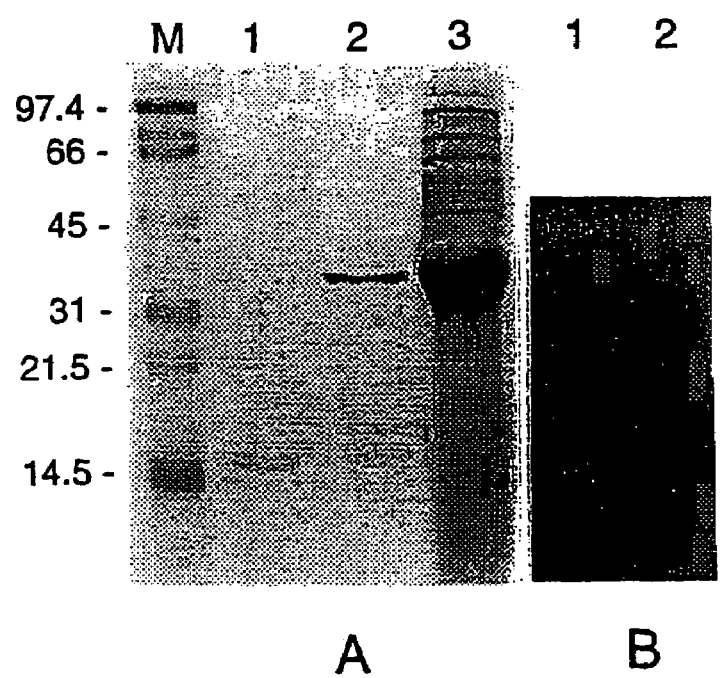

To examine whether the active site is located in the N-terminal domain of AcmA, a DNA fragment starting at codon 58 until codon 218 of acmA was synthesized by PCR and fused to the thioredoxin gene in plasmid pET32A. The fusion protein comprises 326 amino acids. A protein with the expected molecular mass (35 kDa) was isolated from a culture of E. coli BL21(DE3) (pETAcmA) (FIG. 2, lane A2). By cleavage with enterokinase, the protein was split into a thioredoxin part of 17 kDa and an AcmA domain (nA) of 18 kDa (FIG. 2, lane A1). The zymogram (FIG. 2.B) shows that the fusion protein did not have appreciable cell wall hydrolytic activity, while the released domain of AcmA was active (FIG. 2, lanes B1 and B2), indicating that the active site domain was in the N-terminal part of AcmA.

Fusion of the Repeats of AcmA to α-amylase and β-lactamase Yields Active Enzymes.

Figure 3:
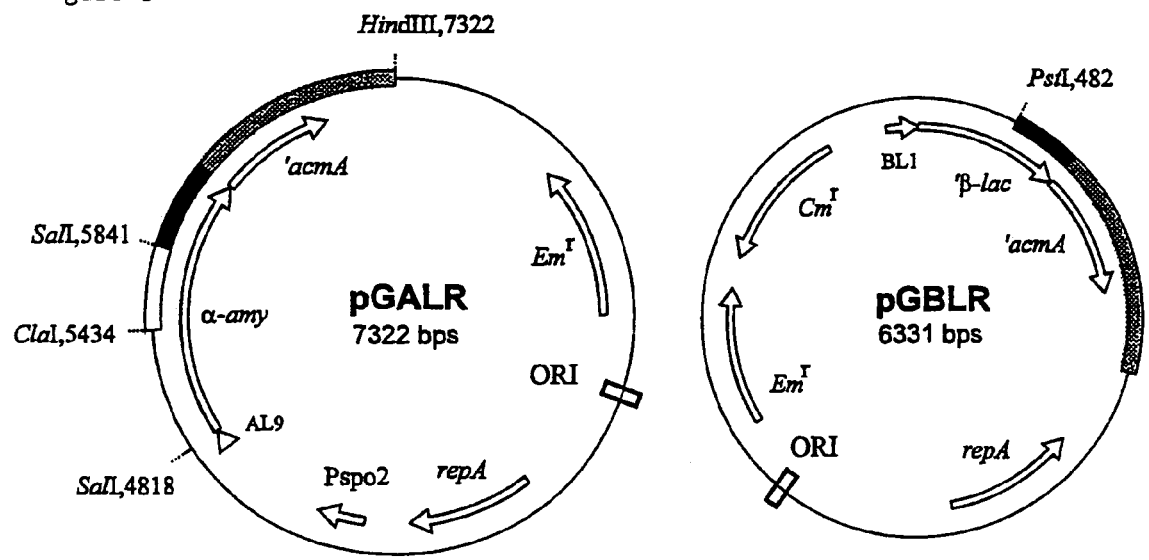
Figure 4:
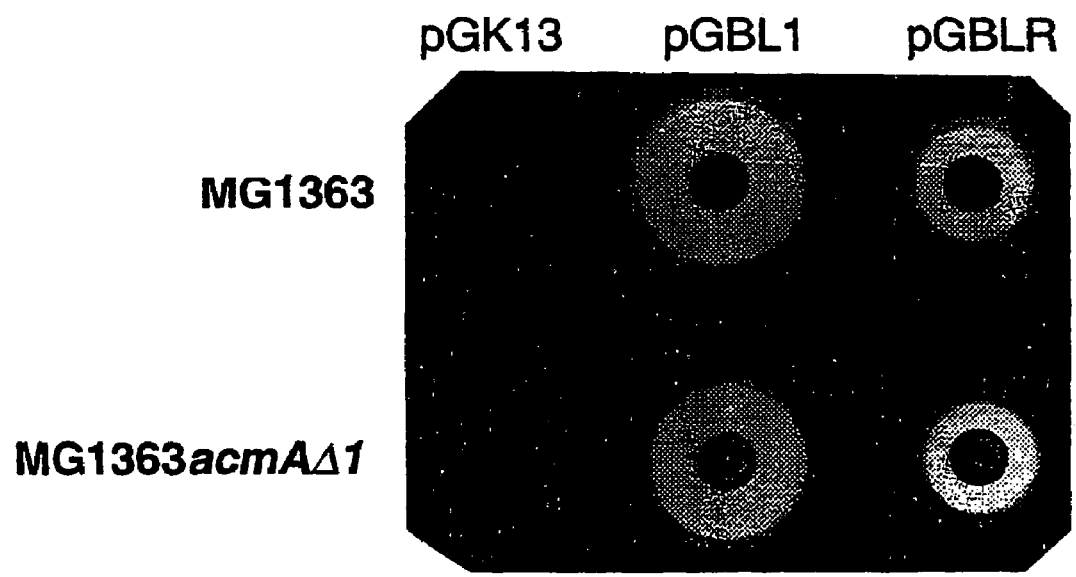

The three C-terminal repeats of AcmA (cA) were fused C-terminally to B. licheniformis α-amylase and E. coli TEM β-lactamase as described in Material and Methods and shown in FIG. 3. The hybrid proteins were fused to the lactococcal signal sequences AL9 and BL1, respectively (21). Both fusion proteins were active in plate assays, as is only shown for the β-lactamase/AcmA fusion protein (βcA) (FIG. 4). The halo's around colonies producing the fusion proteins were smaller than those produced by the wild-type enzymes, which could either be caused by reduced intrinsic enzyme activities due to the presence of repeats or by increased susceptibility to proteolytic degradation. However, the smaller halo's produced by the chimeric proteins might also be caused by hampered diffusion due to cell wall binding (see below).

Figure 5:
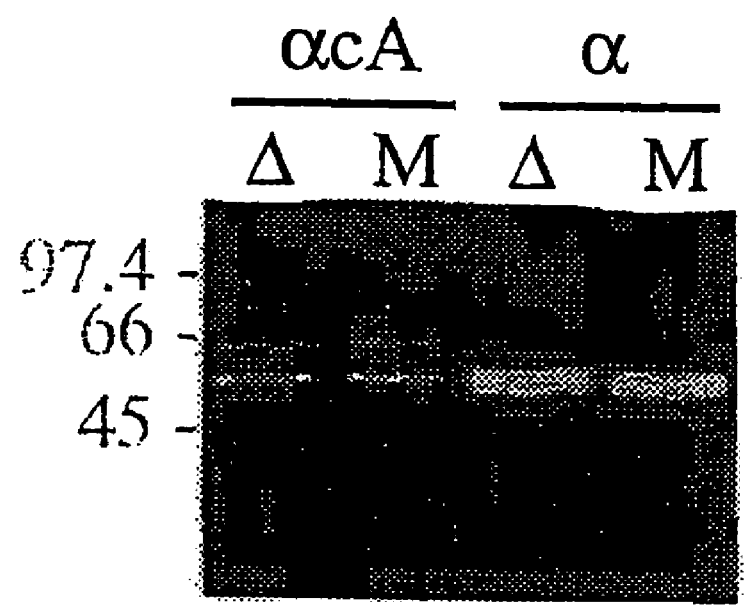

The activities of α-amylase and the αcA fusion protein were also detected in a renaturing SDS-(12.5%)PAA gel containing 1% starch. The primary translation product of the α-amylase gene is a protein of 522 amino acid residues which contains a signal sequence of 37 amino acids (21). It is secreted as a 55-kDa protein. αcA consists of 741 amino acids and, if processed and secreted, would give rise to a 78-kDa protein. Cell and supernatant fractions of L. lactis MG1363 and MG1363acmAΔ1 carrying pGAL9 or pGALR were analyzed after overnight growth of the strains. The results are presented in FIG. 5 and show that the clearing bands are present at the position expected for both mature proteins. Apparently, αcA is active. Clearly, smaller products are present in the supernatants of the cells producing the fusion protein, the smallest being approximately of the size of wild-type mature α-amylase (FIG. 5 and not shown).

The β-lactamase Fusion Protein is Predominantly Present in the Cell Wall.

Figure 6:
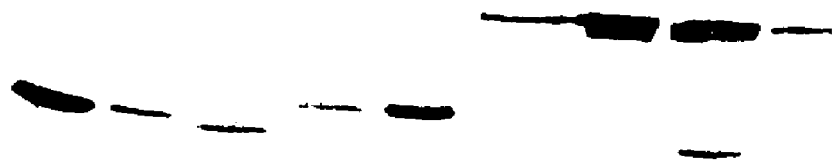

To examine whether the presence of the C-terminal domain of AcmA resulted in binding of βcA to the cell wall, mid-exponential phase cultures of L. lactis MG1363acmAΔ1 containing pGBL1, encoding β-lactamase, or PGBLR, specifying βcA, were fractionated and subjected to Westen blot analysis (FIG. 6). From pGBL1, β-lactamase is expressed as a protein of 322 amino acids containing a signal sequence of 47 amino acids. The secreted protein is 30 kDa. βcA consists of 540 amino acids and is secreted as a protein with a molecular mass of 52 kDa. FIG. 6 shows that most of the wild-type β-lactamase is present in the culture supernatant and none in the cytoplasm. Slightly larger bands, likely representing the unprocessed form, are found in the membrane fractions of this strain. In contrast, βcA is predominantly retained in the cell wall fraction, although a considerable amount resides in the cytoplasm, strongly suggesting that the AcmA repeats anchored the hybrid enzyme to the cell wall. The smaller band present in both cytoplasmic fractions is caused by cross hybridization of the antibodies to an unspecified lactococcal protein (unpublished observation). In the supernatant fraction of cells producing βcA, only little full length protein was observed. Several distinct smaller products are present in this fraction which were also detectable in very low amounts in the cell wall fraction after prolonged exposure of the film (not shown) but were absent from the other fractions.

The C-terminal Repeats in AcmA are Required for Cell Wall Binding.

Although the results presented in the previous section strongly suggests that the C-terminal repeats are required for the retention of protein in the cell wall, definite proof was obtained by mixing the supernatant fractions of end-exponential phase cultures containing AcmA, or one of its deletion derivatives (see FIG. 1), with the cells from an equal volume of a culture of MG1363acmAΔ1 (pGK13). After incubation, cell and supernatant fractions were examined for the presence of AcmA. Except for A0, all proteins were capable of binding to the MG1363acmAΔ1 cells (Table 3). Also, all degradation products of AcmA and its derivatives were capable of binding. The finding that A0 was unable to bind was corroborated by adding the mixture of enterokinase-released nA and thioredoxin to supernatant containing A1. When incubated with AcmA-minus cells, only A1 bound to the lactococcal cells (FIG. 7) as only this protein was detectable in the cell fraction. nA was only detected in the supernatant. This was also the case when the experiment was repeated with nA alone (not shown).

Binding of AcmA or βcA to Lactococcal Cells at Different pHs.

The supernatant fraction of a mid-exponential phase L. lactis MG1363acmAΔ1 culture was replaced by the supernatant of a mid-exponential phase L. lactis MG1363 culture. This mixture was incubated at 30° C. for 5 min. Thereafter the supernatant was removed by centrifugation and the cell pellet was washed with M17. The cell pellets were dissolved in M17 with pHs ranging from 2 to 10 and incubated at 30° C. for 30 min. The cell and supernatant fractions were separated and treated as described before and analysed for the presence of AcmA activity. A similar experiment was executed with mid-exponential phase L. lactis MG1363acmAΔ1 cells with the supernatant of an L. lactis MG1363acmAΔ1(pGBLR) culture. The presence of βcA was analysed by western blotting and immunodetection as described.

At all different pHs, AcmA and βcA was found to be bound to the lactococcal cells. The binding of both AcmA and βcA was better at low pH as judged from the activity in a zymogram and the visual presence of the amount of βcA fusion protein in the cell extracts after immunodetection.

Proteolytic Breakdown of AcmA by Pronase and Trypsin.

The supernatant fraction of a mid-exponential phase MG1363acmAΔ1 culture was replaced by the supernatant of a mid-exponential phase MG1363 culture. This mixture was incubated at 30° C. for 15 min. Thereafter the supernatant and the cell fractions were separated and the cell pellet was dissolved in an identical volume of M17. To both fractions Pronase and Trypsin (1 mg/ml) dissolved in 10 mM NaPi buffer (pH=7) was added to an end concentration of (10 μg/ml) and the mixtures were incubated at 30° C. Samples were taken after 5 and 30 min and 2 h of incubation. The cell and supernatant fractions of each sample were separated and prepared for zymographic analysis as described above.

A complete hydrolysis of AcmA by pronase was observed in the supernatant fraction after 2 h of incubation while activity was still present in the cell extract at this time point. The hydrolysis of AcmA by trypsin was slower and activity was still present in the supernatant after 2 h of incubation. In time the portion of activity present in the cell extracts was always higher than that observed in the supernatant. These results indicate that the AcmA protein is protected when it is bound to the cell.

Binding of AcmA to Different Types of Bacterial Cells.

The strains Bacillus subtilis DB104, Lactobacillus plantarum 80, Streptococcus faecalis JH2-2, Streptococcus thermophilus ATCC 19258, Listeria P, Lactobacillus buchneeri L4, Clostridium beijerinckii CNRZ 530 and Escherichia coli NM522 were grown overnight in GM17. Two fractions of each overnight culture were centrifuged and the supernatants were replaced by the supernatant of an overnight-culture of L. lactis MG1363acmAΔ1 (pGKAL1) or MG1363acmAΔ1 (pGK13). The mixtures were incubated at 30° C. for 15 min. Subsequently the cell and supernatant fractions were separated and the cells were washed once with M17 and were prepared for SDS-PAGE as described before and analysed for AcmA activity.

In all cell extracts AcmA activity was present while such an activity was absent in extracts of cells which had been incubated with the supernatant of MG1363acmAΔ1 (pGK13) which lacks the presence of AcmA.

To investigate the effect of repeat number on binding, equal volumes of the supernatants of cultures of MG1363acmAΔ1 (pGKAL3, encoding A2) and MG1363acmAΔ1 (pGKAL4, specifying A1) were mixed. The undiluted and a 10-fold diluted mixture were incubated with the AcmA-free cells. Analysis of zymograms of serial dilutions showed that the two activities were equally distributed over the cell and supernatant fractions, indicating that both proteins bind equally well (results not shown).

Figure 8:
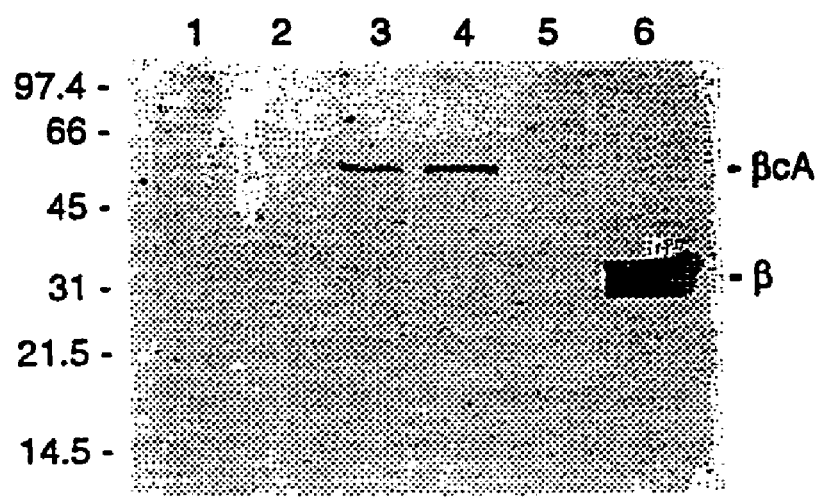

To examine whether the C-terminal repeat sequences of AcmA had the capacity to bind a heterologous, extracellular enzyme to lactococcal cells, binding of βcA was assessed by incubation of AcmA-minus L. lactis cells with culture supernatants containing either secreted wild-type β-lactamase or βcA. As FIG. 8 shows, wild-type β-lactamase was exclusively present in the supernatant fraction, whereas βcA fractionated with the lactococcal cells and, thus, had bound to these cells.

DISCUSSION

The results presented in this work indicate that the mature form of the N-acetylmuramidase AcmA of L. lactis consists of two separate domains. The overproduced and purified N-terminus, from amino acid residue 58 to 218 in the pre-protein, is active on M. lysodeikticus cell walls and, thus, contains the active site of the enzyme. This is in agreement with the finding that the repeat-less AcmA mutant A0 can still hydrolyze M. lysodeikticus cell walls, albeit with severely reduced efficiency. Prolonged renaturation was needed to detect the activity of the enzyme in vitro while colonies producing the protein did not form a halo. Enzymes A1 and A2 had in vitro activities which were nearly the same as that of the wild-type protein, although in the plate assay A1 produced a smaller halo than A2 which, in turn, was smaller than the wild-type halo. A strain producing A1 grew in longer chains than cells expressing A2 and, in contrast to A2 producing cells, sedimented and did not autolyze. Taken together these results indicate that, although the N-terminus of AcmA contains the active site, the presence of at least one complete repeat is needed for the enzyme to retain appreciable activity. Second, only cultures producing AcmA's containing two or more full length repeats are subject to autolysis and produce wild-type chain lengths. It is tempting to speculate that this apparent increase in catalytic efficiency of AcmA is caused by the repeat domain by allowing the enzyme to bind to its substrate, the peptidoglycan of the cell wall. As was postulated by Knowles et al. (12) for the cellulase binding domains in cellobiohydrolases, such binding would increase the local concentration of the enzyme. The repeats could be involved in binding alone or could be important for proper positioning of the catalytic domain towards its substrate. The increase in AcmA activity with an increasing number of repeats to up to 3 in the wild-type enzyme, suggests an evolutionary process of repeat amplification to reach an optimum for proper enzyme-functioning. The binding of A1, A1.5 and A4 was comparable with that of wild-type AcmA but these enzyme varieties caused no or only little autolysis. These observations seem to support the idea that 3 repeats are optimal for proper functioning of AcmA. The presence of 5 and 6 repeats in the very similar enzymes of E. faecalis and E. hirae, respectively, may reflect slight differences in cell wall structure and/or the catalytic domain, requiring the recruitment by these autolysins of extra repeats for optimal enzyme activity.

The hypothesis that the C-terminal domain of AcmA is involved in cell binding (6) was corroborated in this study. First of all we show that AcmA is indeed capable of cell binding. AcmA and its derivatives A1, A1.5, A2 and A4 all bound to cells of L. lactis when added from the outside. To prove that it was the C-terminus of AcmA that facilitated binding and not some intrinsic cell wall binding capacity of the N-terminal domain, the repeat domain was fused to two heterologous proteins which do not normally associate with the cell wall. The smaller halo's produced by αcA and βcA compared to the wild-type proteins and the presence of most of βcA in the cell wall fraction are indicative of cell binding of the fusion proteins via the AcmA-specific repeats.

The βcA binding studies clearly show that it is the AcmA repeat domain that specifies cell wall binding capacity: whereas wild-type β-lactamase (and, for that matter, repeat-less AcmA) did not bind to lactococcal cells, βcA did bind to these cells when added from the outside. The results obtained with A1 in the binding assay show that only one repeat is sufficient to allow efficient binding of AcmA. In a separate study (5) we showed that AcmA can operate intercellularly: AcmA-free lactococcal cells can be lyzed when grown together with cells producing AcmA. Combining this observation with the results presented above allows to conclude that AcmA does not only bind when confronting a cell from the outside but, indeed, is capable of hydrolyzing the cell wall with concomitant lysis of the cell.

AcmA-like repeats were found to be present at different locations in more than 30 proteins after a comparison of the amino acid sequences of the repeats in AcmA with the protein sequences of the Genbank database (release 23). Not all of these proteins with repeats varying from one to six are cell wall hydrolases. Alignment of the amino acid sequences of all the repeats yielded a consensus sequence similar to that postulated by Birkeland and Hourdou et al. (4, 9). Interestingly, if a limited number of modifications are allowed in the consensus repeat, the repeat is also present 12 and 4 times, respectively, in two proteins of Caenorhabditis elegans, which both show homology with endochitinases (Gene accession numbers U64836 and U70858) (36). Possibly, these repeats anchor these enzymes to fungi ingested by this organism. The presence of similar repeats in proteins of different bacterial species strongly suggests that they recognize and bind to a general unit of the peptidoglycan. An interesting goal for the future will be to elucidate the unit to which they bind and the nature of the binding.

As has been reported earlier for intact AcmA (5), and, as we show here for its C-terminal deletion derivatives, the enzyme is subject to proteolytic degradation. None of the degradation products were present in cell extracts of whole cells indicating that they are not formed inside the cell (data not shown). The degradation pattern of each AcmA derivative is specific and very reproducible. Based on the sizes of the degradation products, a number of the proteolytic cleavage sites probably resides in the intervening sequences. One such site (1 in FIG. 1) is present between repeat 1 and 2. Cleavage at this position would result in an active protein of approximately 28 kDa, which is indeed seen in the supernatants of all strains producing AcmA with 1.5 or more repeats. A second cleavage site is probably located between the second and third repeat (2 in FIG. 1). Cleavage at this site is either rather infrequent, or the resulting degradation product is not very active, which, in both cases, would lead to the faint bands of activity observed in lanes 1 and 3 of the zymogram presented in FIG. 1. The presence of cleavage sites in between the AcmA repeats is further suggested by the presence of specific degradation products observed in αcA and μcA; their sizes are in accord with the location of the cleavage sites postulated in AcmA. In addition, as also bands of the size of the wild-type α-amylase and β-lactamase are observed, an additional cleavage site seems to be present around the fusion point of these enzymes and the cell wall binding domain of AcmA.

All degradation products of AcmA and those of the two fusion proteins are mainly present in the supernatant and to some extent in the cell wall fraction, but not in the cells. As none of the *L. lactis* strains used produced the cell wall-anchored proteinase PrtP, this enzyme can not be held responsible for the specific degradation of AcmA or the fusion proteins. Apparently, an extracellular proteinase exists in *L. lactis* that is capable of removing the repeats, which may represent a mechanism for the regulation of AcmA activity.

TABLE 1

Bacterial strains and plasmids used in this study.

| Strain or plasmid | Relevant phenotype(s) or genotype(s) | Source or reference |
| --- | --- | --- |
| Strains | | |
| *L. lactis* subsp. *cremoris* | | |
| MG1363 | Plasmid-free strain | (8) |
| MG1363 acmAΔ1 | Derivative of MG1363 carrying a 701-bp SacI-SpeI deletion in acmA | (6) |
| *E. coli* | | |
| NM522 | supE thi Δ(lac-proAB) Δhsd5($r_k^-$,$m_k^-$) [F' proAB lacI$^q$ZM15] | Stratagene |
| BL21 (DE3) | ompT $r_B^- m_B^-$ int; bacteriophage DE3 lysogen carrying the T7 RNA polymerase gene controlled by the lacUV5 promoter | (30) |
| Plasmids | | |
| pET32A | Ap$^r$, vector for high level expression of thioredoxin fusion proteins | Novagen |
| pUK21 | Km$^r$, general cloning vector | (35) |
| pBluescript SK+ | Ap$^r$, general cloning vector | Stratagene |
| pAL01 | Ap$^r$, pUC19 carrying a 4,137-bp lactococcal chromosomal DNA insert with acmA gene | (6) |
| pDEL1 | Ap$^r$, pBluescript SK+ with 785-bp SacI-EcoRI fragment of acmA obtained by PCR with primers ALA-4 and REPDEL-1 | This work |
| pDEL2 | Ap$^r$, pBluescript SK+ with 554-bp SacI-EcoRI fragment of acmA obtained by PCR with primers ALA-4 and REPDEL-2 | This work |
| pDEL3 | Ap$^r$, pBluescript SK+ with 348-bp SacI-EcoRI fragment of acmA obtained by PCR with primers ALA-4 and REPDEL-3 | This work |
| pGKAL1 | Em$^r$, Cm$^r$, pGK13 containing acmA under control of its own promoter on a 1,942-bp SspI-BamHI insert | (5) |
| pGKAL3 | Em$^r$, Cm$^r$, pGKAL1 derivative expressing A2 | This work |
| pGKAL4 | Em$^r$, Cm$^r$, pGKAL1 derivative expressing A1 | This work |
| pGKAL5 | Em$^r$, Cm$^r$, pGKAL1 derivative expressing A0 | This work |
| pGKAL6 | Em$^r$, Cm$^r$, pGKAL1 derivative expressing A1.5 | This work |
| pGKAL7 | Em$^r$, Cm$^r$, pGKAL1 derivative expressing A4 | This work |
| pETAcmA | Ap$^r$, pET32A expressing active site domain of AcmA from residues 58 to 218 fused to thioredoxin | This work |
| pGBL1 | Em$^r$, pWV01 derivative expressing *E. coli* TEM-β-lactamase fused to export element BL1 of *L. lactis* | (21) |
| pGAL9 | Em$^r$, pWV01 derivative expressing *B. licheniformis* α-amylase fused to export element AL9 of *L. lactis* | (21) |
| pUKAL1 | Km$^r$, pUK21 with ±1,050-bp ClaI-HindIII fragment of pGAL9 | This work |
| pUKAL2 | Km$^r$, pUKAL1 in which the ±650-bp SalI-EcoRV fragment is replaced by the 440-bp SalI-EcoRV fragment of the PCR fragment obtained with primers ALFA-A and -B | This work |
| pUKALR | Km$^r$, pUKAL2 with 1,104-bp PvuII-XbaI fragment of pAL01 in EcoRV and XbaI sites | This work |
| pUKblac | Km$^r$, pUK21 with 311-bp PstI-NdeI PCR fragment obtained with primers BETA-1 and -2 | This work |
| pUKblacR | Km$^r$, pUKblac carrying 1,104-bp PvuII-XbaI fragment of pAL01 in NdeI and XbaI sites | This work |
| pGBLR | Em$^r$, pGBL1 expressing the β-lactamase/AcmA fusion protein | This work |
| pGALR | Em$^r$, pGAL9 expressing the α-amylase/AcmA fusion protein | This work |

| Name | Nucleotide Sequence (5'→3') | R/E Site |
|---|---|---|
| REPDEL-1 | CGCGAATTCAGATTATGAAACAATAAG SEQ ID NO: 1 | EcoRI |
| REPDEL-2 | CGCGAATTCTTATGTCAGTACAAGTTTTTG SEQ ID NO: 2 | EcoRI |
| REPDEL-3 | CGCGAATTCCTTATGAAGAAGCTCCGTC SEQ ID NO: 3 | EcoRI |
| ALA-4 | CTTCAACAGACAAGTCC SEQ ID NO: 4 | |
| REP-4A | AGCAATACTAGTTTTATA SEQ ID NO: 5 | SpeI |
| REP-4B | CGCGAATTCGCTAGCGTCGCTCAAATTCAAAGTGCG SEQ ID NO: 6 | NheI |
| ACMHIS | AGGAGATCTGCGACTAACTCATCAGAGG SEQ ID NO: 7 | BglII |
| BETA-1 | GGATCATGTAACTCGCC SEQ ID NO: 8 | |
| BETA-2 | GGAATTCCATATGCTTAATCAGTGAGG SEQ ID NO: 9 | NdeI |
| ALFA-A | GCATCCGTTGAAAGCGG SEQ ID NO: 10 | |
| ALFA-B | GAATTCGATATCTTTGAACATAAATTG SEQ ID NO: 11 | EcoRV |
| ALA-14 | GATAAATGATTCCAAGC SEQ ID NO: 12 | |
| ALA-22 | CTCAAATTCAAAGTGCG SEQ ID NO: 13 | |

TABLE 3

Properties of *L. lactis* expressing AcmA derivatives.

| Number[a] | Strain (plasmid)[b] | AcmA variant[c] | % Reduction in $OD_{600}$[d] | PepX activity[e] | Chain length[f] | Halo[g] | Sedimentation[h] | AcmA activity[i] sup | AcmA activity[i] ce | Cell binding[j] |
|---|---|---|---|---|---|---|---|---|---|---|
| 1 | MGpGK13 | A3 | 32.6 | 16.9 | A | 3.1 | − | + | + | + |
| 2 | Δ1pGK13 | — | 15.2 | 0.3 | C | 0 | + | − | − | − |
| 3 | Δ1pGKAL1 | A3 | 36.7 | 19.8 | A | 5.0 | − | + | + | + |
| 4 | Δ1pGKAL3 | A2 | 29.3 | 13.3 | A | 4.6 | − | + | + | + |
| 5 | Δ1pGKAL4 | A1 | 18.8 | 0.4 | B | 3.9 | + | + | + | + |
| 6 | Δ1pGKAL5 | A0 | 15.6 | 0.3 | C | 0 | + | + | − | − |
| 7 | Δ1pGKAL6 | A1.5 | 18.6 | 1.6 | B | 2.2 | ± | + | + | + |
| 8 | Δ1pGKAL7 | A4 | 21.1 | 4.9 | A | 4.0 | − | + | + | + |

[a] The number corresponds to the AcmA derivative produced, as schematized in FIG. 1.
[b] MG: *L. lactis* MG1363, Δ1: *L. lactis* MG1363acmAΔ1.
[c] —: no AcmA produced; Ax: AcmA with x repeats.
[d] The $OD_{600}$ reduction was calculated using the following formula: $[(OD_{max.} - OD_{60\ hours})/OD_{max.}] * 100\%$.
[e] Activity is in arbitrary units measured as the increase of absorption at 405 nm in time.
[f] End exponential phase ½M17 cultures were subjected to light microscopic analysis.
A: mainly single cells and some chains up to 5 cells
B: some single cells but mainly chains longer than 5 cells
C: no single cells, only very long chains
[g] The sizes of the halo's were measured in millimeters from the border of the colony after 45 h of incubation at 30° C.
[h] Analyzed by visual inspection of standing ½M17 cultures after overnight growth in test tubes.
[i] Judged from zymograms of samples from end-exponential phase ½M17 cultures; sup: supernatant fraction, ce: cell-extract.
[j] Binding of AcmA derivatives in supernatants of end-exponential phase 1/2 M17 cultures to end-exponential phase cells of *L. lactis* MG1363acmAΔ1 after 20 min of incubation at 30° C. (see text for details).

FIG. 1. Analysis of AcmA activity in supernatant fractions of end-exponential-phase cultures of MG1363 containing pGK13 (1) and MG1363acmAΔ1 containing either pGK13, not encoding AcmA (2), pGKAL1, encoding enzyme A3 (3), pGKAL3, encoding enzyme A2 (4), pGKAL4, encoding enzyme A1 (5), pGKAL5, encoding enzyme A0 (6), pGKAL6, encoding enzyme A1.5 (7), or pGKAL7, encoding enzyme A4 (8) in a renaturing SDS-(12.5%)PAA gel containing 0.15% *M. lysodeikticus* autoclaved cells. Molecular masses (in kilodaltons, kDa) of standard proteins (lane M) are shown in the left margin. Below the gel the lower part of lanes 5, 6 and 7 of the same gel is shown after one week of renaturation. The right half of the figure gives a schematic representation of the various AcmA derivatives. SS (black), signal sequence; Rx (dark grey), repeats; light grey, Thr, Ser and Asn-rich intervening sequences (6); arrows, artificially duplicated region in the AcmA derivative containing four repeats. The active site domain is shown in white. MW, expected molecular sizes in kDa of the secreted forms of the AcmA derivatives. The numbers of the AcmA derivatives correspond with the lane numbers of the gel. Numbered arrowheads indicate the putative location of proteolytic cleavage sites.

FIG. 2. Purification of the AcmA active site domain (nA). (A) SDS-(12.5%) PAGE of cell extract of 10 μl of *E. coli* BL21(DE3) (pETAcmA) (lane 3) induced for 4 h with IPTG. Lane 2, 10 μl of purified fusion protein isolated from 25 μl of induced *E. coli* culture and lane 1, 10 μl of the enterokinase cleft protein. (B) Renaturing SDS-(12.5%) PAGE with 0.15% *M. lysodeikticus* autoclaved cells using the same amount of the samples 1 and 2 shown in part A. Molecular masses (in kilodaltons) of standard proteins are shown on the left of the gel. Before loading the samples were mixed with an equal volume of 2× sample buffer (15).

FIG. 3. Schematic representation of plasmids pGBLR and pGALR carrying, respectively, C-terminal fusions of the repeats of AcmA to β-lactamase and α-amylase. α-amy, α-amylase gene of *B. licheniformis*; β-lac, β-lactamase gene of *E. coli*; acmA, 3-prime end of the N-acetylmuramidase gene of *L. lactis* MG1363 encoding the three repeats; EmR and CmR, erythromycin and chloramphenicol resistance genes; AL9 and BL1, protein secretion signals from *L. lactis* MG1363 (21); repA and ORI, gene for the replication protein and origin of replication of the lactococcal plasmid pWV01, respectively; Pspo2, *B. subtilis* phage Spo2 promoter. Black boxes indicate the PCR fragments used for the introduction of the restriction enzyme sites EcoRV and NdeI at the position of the stopcodons of the α-amylase and β-lactamase genes, respectively. The open box indicates the part which has been subcloned into pUK21 for construction work. The grey boxes show the fragment of pAL01 used to fuse the 3'-end of acmA to the α-amylase and β-lactamase genes. Only relevant restriction enzyme sites are shown.

FIG. 4. β-lactamase activity in *L. lactis*. Activity of wild-type β-lactamase and its AcmA fusion derivative (βcA) produced by cells of *L. lactis* MG1363 and MG1363acmAΔ1 containing pGK13, pGBL1 or PGBLR. The ½M17 agar plate was stained with iodine after overnight growth of the colonies according the protocol of Smith et al. (29).

FIG. 5. α-amylase activity in the supernatant of *L. lactis*. Activity of wild-type α-amylase (α) and the αcA fusion protein in an SDS-(12.5%)PAA gel containing 1% starch. The proteins were renatured by washing the gel with Triton X-100 and subsequently stained with iodine (33). The equivalent of 40 μl of supernatant of ½M17 cultures of *L. lactis* MG1363 (M) and MG1363acmAΔ1 (A) containing pGAL9 or pGALR were loaded onto the gel. Molecular masses (in kDa) of standard proteins are shown in the left margin.

FIG. 6. Localization of β-lactamase in *L. lactis*. Western blot analysis of fractions of MG1363acmAΔ1 expressing β-lactamase (from pGBL1) or βcA fusion protein (encoded by PGBLR) using polyclonal antibodies directed against β-lactamase. Amount of samples loaded is equal to 200 μl of culture. Fractions: S, supernatant; CW, cell wall; CY, cytoplasm; MB, membrane-associated; and M, membrane.

Figure 7:
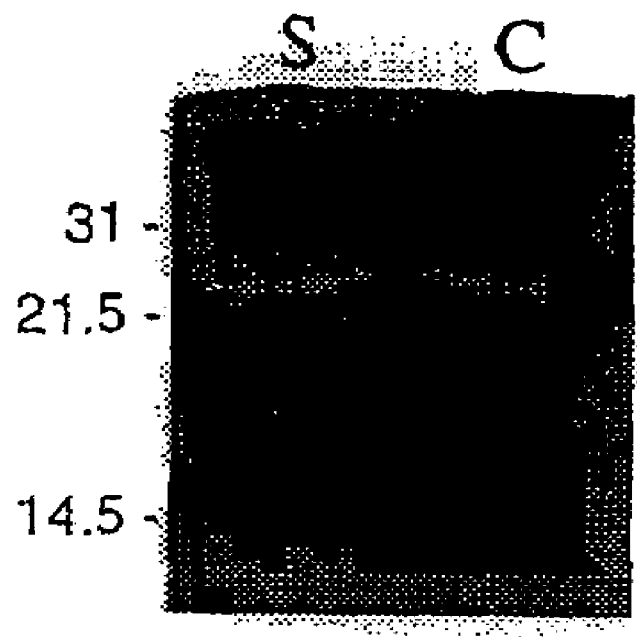

FIG. 7. Analysis of the binding of AcmA derivatives nA and A1 by a renaturing SDS-(17.5%) PAGE with 0.15% *M. lysodeikticus* autoclaved cells. Cell (C) and supernatant (S) fractions of MG1363acmAΔ1 cells incubated with nA and A1 from the culture supernatant of MG1363acmAΔ1 containing pGKAL4. 60 μl of the samples were loaded. Molecular masses (in kDa) of standard proteins are shown in the left margin.

FIG. 8. Binding of the βcA fusion protein to *L. lactis*. The figure shows a Western blot using polyclonal antibodies against β-lactamase. Cell extracts (lanes 1, 3, 5) and supernatants (lanes 2, 4, 6) of mid-exponential phase MG1363acmAΔ1 (pGK13) cells incubated for 5 minutes with supernatants of MG1363acmAΔ1 containing pGK13 (lanes 1, 2), pGBLR (lanes 3, 4) or pGBL1 (lanes 5, 6), respectively. The positions of wild-type β-lactamase (β) and the βcA fusion protein are indicated on the right. Molecular masses (in kDa) of standard proteins are shown in the left margin. Twenty μl of samples were loaded onto an 12.5% PAA gel.

Figure 9:
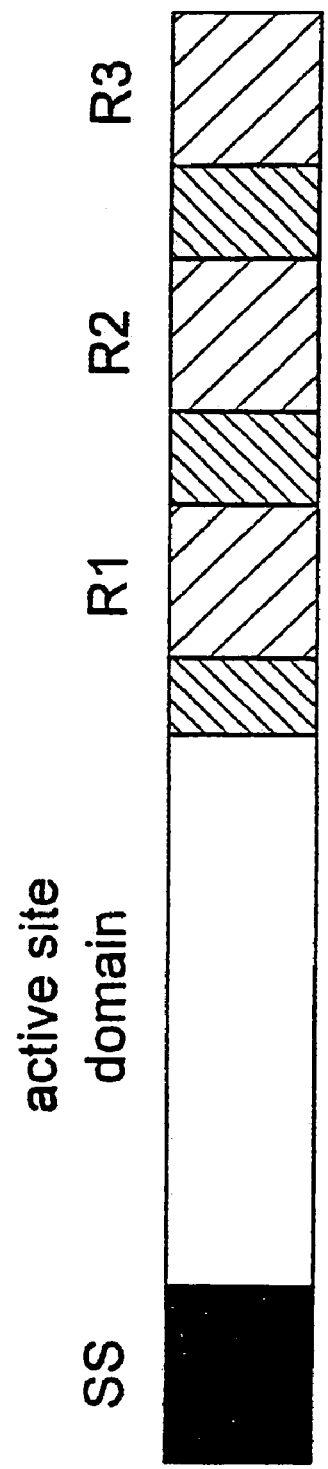

FIG. 9. Schematic representation of the AcmA protein. SS (black), signal sequence; R (dark grey), repeats; shaded regions, intervening sequences. The active site domain is shown in white.

FIG. 10. Amino acid sequence alignment of the repeats of AcmA in *L. lactis* plus consensus sequence. Amino acid sequences SEQ ID NO: 14, SEQ ID NO: 15, SEQ ID NO: 16, and SEQ ID NO: 17 are depicted.

FIG. 11. Amino acid sequence alignment of repeats in various (SEQ ID NO: 20 through SEQ ID NO: 110), wherein:

| SEQ ID NO: | Species and Protein | Residue No. |
| --- | --- | --- |
| SEQ ID NO: 20 | *Lactobacillus lactis* acmA | 245–287 (33) |
| SEQ ID NO: 21 | | 321–363 (31) |
| SEQ ID NO: 22 | | 395–437 |
| SEQ ID NO: 23 | *Enterococcus faecalis* autolysin | 363–405 (25) |
| SEQ ID NO: 24 | | 431–473 (25) |
| SEQ ID NO: 25 | | 499–541 (25) |
| SEQ ID NO: 26 | | 567–609 (19) |
| SEQ ID NO: 27 | | 629–671 |
| SEQ ID NO: 28 | *Enterococcus hirae* mur2 | 257–299 (38) |
| SEQ ID NO: 29 | | 338–380 (33) |
| SEQ ID NO: 30 | | 414–456 (32) |
| SEQ ID NO: 31 | | 489–531 (33) |
| SEQ ID NO: 32 | | 565–607 (15) |
| SEQ ID NO: 33 | | 623–665 |
| SEQ ID NO: 34 | *Lactococcus* øTuc2009 lys | 332–375 (10) |
| SEQ ID NO: 35 | | 386–428 |
| SEQ ID NO: 36 | *Lactococcus* ø-LC3 lysB | 333–376 (10) |
| SEQ ID NO: 37 | | 387–429 |
| SEQ ID NO: 38 | *Bacillus* øPBSX xy1A | 161–204 |
| SEQ ID NO: 39 | *Bacillus* ø PZA orf 15 | 163–207 (6) |
| SEQ ID NO: 40 | (=ø–29) | 214–258 |
| SEQ ID NO: 41 | *Bacillus* ø B103 orf 15 | 165–209 (9) |
| SEQ ID NO: 42 | | 219–263 |
| SEQ ID NO: 43 | *Bacillus* øgle lys | 399–442 |
| SEQ ID NO: 44 | *Bacillus sphaericus* Pep I | 3–46 (6) |
| SEQ ID NO: 45 | | 53–96 |
| SEQ ID NO: 46 | *Haemophilus influenzae* amia | 294–336 |
| SEQ ID NO: 47 | | 387–430 |
| SEQ ID NO: 48 | *Listeria monocytogenes* P60 | 30–72 (130) |
| SEQ ID NO: 49 | | 203–245 |
| SEQ ID NO: 50 | *Listeria innocua* P60 | 30–72 (130) |
| SEQ ID NO: 51 | | 201–243 |
| SEQ ID NO: 52 | *Listeria ivanovii* P60 | 30–72 (125) |
| SEQ ID NO: 53 | | 198–240 |
| SEQ ID NO: 54 | | 314–356 |
| SEQ ID NO: 55 | *Listeria seeligeri* P60 | 30–72 (127) |
| SEQ ID NO: 56 | | 200–242 (75) |
| SEQ ID NO: 57 | | 320–362 |
| SEQ ID NO: 58 | *Listeria welshimeri* P60 | 30–72 (127) |
| SEQ ID NO: 59 | | 198–240 (75) |
| SEQ ID NO: 60 | | 316–358 |
| SEQ ID NO: 61 | *Listeria grayi* P60 | 30–72 (104) |
| SEQ ID NO: 62 | | 177–219 (79) |
| SEQ ID NO: 63 | | 299–342 |
| SEQ ID NO: 64 | *Escherichia coli* yebA | 77–121 |
| SEQ ID NO: 65 | *Haemophilus influenzae* yebA | 131–174 |
| SEQ ID NO: 66 | *Escherichia coli* nlpD | 123–166 |
| SEQ ID NO: 67 | *Haemophilus influenzae* lppB | 147–190 |
| SEQ ID NO: 68 | *Haemophilus somnus* lppB | 120–164 |
| SEQ ID NO: 69 | *Pseudomonas aeruginosa* lppB | 69–113 |
| SEQ ID NO: 70 | *Synechocystis* nlpD | 187–130 |
| SEQ ID NO: 71 | *Sinohizobium meliloti* nlpD | 166–209 |
| SEQ ID NO: 72 | *Escherichia coli* dniR | 113–155 (16) |
| SEQ ID NO: 73 | | 172–213 |
| SEQ ID NO: 74 | *Staphylococcus aureus* ProtA | 431–474 |
| SEQ ID NO: 75 | *Bacillus subtilis* papQ | 28–70 (17) |
| SEQ ID NO: 76 | | 88–130 (20) |
| SEQ ID NO: 77 | | 151–193 |
| SEQ ID NO: 78 | *Bacillus subtilis* spoVID | 525–568 |
| SEQ ID NO: 79 | *Escherichia coli* | 50–93 |
| SEQ ID NO: 80 | *Synechocystis* | 4–47 |
| SEQ ID NO: 81 | *Bacillus subtilis* yaaH | 1–43 (5) |
| SEQ ID NO: 82 | | 49–92 |
| SEQ ID NO: 83 | *Bacillus subtilis* yhdD | 29–71 |
| SEQ ID NO: 84 | | 94–136 (29) |
| SEQ ID NO: 85 | | 176–218 (23) |
| SEQ ID NO: 86 | | 242–284 (24) |
| SEQ ID NO: 87 | | 309–353 |
| SEQ ID NO: 88 | *Caenorhabditis elegans* | 23–66 (11) |
| SEQ ID NO: 89 | | 78–121 (21) |

-continued

| SEQ ID NO: | Species and Protein | Residue No. |
|---|---|---|
| SEQ ID NO: 90 | | 143–186 (21) |
| SEQ ID NO: 91 | | 208–251 (19) |
| SEQ ID NO: 92 | | 271–314 (20) |
| SEQ ID NO: 93 | | 335–378 (23) |
| SEQ ID NO: 94 | | 402–445 (21) |
| SEQ ID NO: 95 | | 467–510 (37) |
| SEQ ID NO: 96 | | 548–591 (44) |
| SEQ ID NO: 97 | | 636–679 (66) |
| SEQ ID NO: 98 | | 746–786 (8) |
| SEQ ID NO: 99 | | 795–838 |
| SEQ ID NO: 100 | Caenorhabditis elegans | 23–66 (51) |
| SEQ ID NO: 101 | | 118–161 (25) |
| SEQ ID NO: 102 | | 187–226 (9) |
| SEQ ID NO: 103 | | 236–279 |
| SEQ ID NO: 104 | Bacillus subtilis | 191–136 |
| SEQ ID NO: 105 | Citrobacter fruendii eae | 65–113 |
| SEQ ID NO: 106 | Escherichia coli eae | 65–113 |
| SEQ ID NO: 107 | Bacillus subtilis yneA | 40–90 |
| SEQ ID NO: 108 | Streptococcus pyogenes | 47–103 |
| SEQ ID NO: 109 | Bacillus subtilis yqbp | 177–234 |
| SEQ ID NO: 110 | Bacillus subtilis | 161–218 | a) Proteins listed were obtained by a homology search in the SWIS-SPROT, PIR, and Genbank databases with the repeats of AcmA using the BLAST program (1).
b) *; genes encoding cell wall hydrolases. #; proteins containing repeats that are longer than average.
c) The number of amino acid residues between the repeats are given between brackets.
d) Number of amino acids of the primary translation product.
e) Genbank accession number.

REFERENCES

1. Altschul, S. F., W. Gish, W. Miller, E. W. Myers, and D. J. Lipman. 1990. Basic local alignment search tool. J. Mol. Biol. 215:403–410.
2. Baankreis, R. 1992. The role of lactococcal peptidases in cheese ripening. PhD Thesis. University of Amsterdam, the Netherlands.
3. Béliveau, C., C. Potvin, J. Trudel, A. Asselin, and G. Bellemare. 1991. Cloning, sequencing, and expression in Escherichia coli of a Streptococcus faecalis autolysin. J. Bacteriol. 173:5619–5623.
4. Birkeland, N.-K. 1994. Cloning, molecular characterization, and expression of the genes encoding the lytic functions of lactococcal bacteriophage ØLC3: a dual lysis system of modular design. Can. J. Microbiol. 40:658–665.
5. Buist, G., H. Karsens, A. Nauta, D. Van Sinderen, G. Venema, and J. Kok. 1997. Autolysis of Lactococcus lactis caused by induced overproduction of its major autolysin AcmA. Appl. Environ. Microbiol. 63: 2722–2728
6. Buist, G., J. Kok, K. J. Leenhouts, M. Dabrowska, G. Venema, and A. J. Haandrikman. 1995. Molecular cloning and nucleotide sequence of the gene encoding the major peptidoglycan hydrolase of Lactococcus lactis, a muramidase needed for cell separation. J. Bacteriol. 177: 1554–1563.
7. García, J. L., E. Díaz, A. Romero, and P. García. 1994. Carboxy-terminal deletion analysis of the major pneumococcal autolysin. J. Bacteriol. 176:4066–4072.
8. Gasson, M. J. 1983. Plasmid complements of Streptococcus lactis NCDO 712 and other lactic Streptococci after protoplast-induced curing. J. Bacteriol. 154:1–9.
9. Hourdou, M.-L., M. Guinand, M.-J. Vacheron, G. Michel, L. Denoroy, C. Duez, S. Englebert, B. Joris, G. Weber, and J.-M. Ghuysen. 1993. Characterization of the sporulation-related γ-D-glutamyl-(L)meso-diaminopimelic-acid-hydrolysing peptidase I of Bacillus sphaericus NCTC 9602 as a member of the metallo(zinc) carboxypeptidase A family (Modular design of the protein). Biochem. J. 292:563–570.
10. Joris, B., S. Englebert, C. P. Chu, R. Kariyama, L. Daneo-Moore, G. D. Shockman, and J. M. Ghuysen. 1992. Modular design of the Enterococcus hirae muramidase-2 and Streptococcus faecalis autolysin. FEMS Microbiol. Lett. 91:257–264.
11. Kariyama, R. and G. D. Shockman. 1992. Extracellular and cellular distribution of muramidase-2 and muramidase-1 of Enterococcus hirae ATCC 9790. J. Bacteriol. 174:3236–3241.
12. Knowles, J., P. Lehtovaara, and T. Teeri. 1987. Cellulase families and their genes. Tibtech. 5:255–261.
13. Kuroda, A. and J. Sekiguchi. 1990. Cloning, sequencing and genetic mapping of a Bacillus subtilis cell wall hydrolase gene. J. Gen. Microbiol. 136:2209–2216.
14. Kuroda, A., Y. Sugimoto, T. Funahashi, and J. Sekiguchi. 1992. Genetic structure, isolation and characterization of a Bacillus licheniformis cell wall hydrolase. Mol. Gen. Genet. 234:129–137.
15. Laemmli, U. K. 1970. Cleavage of structural proteins during the assembly of the head of bacteriophage T4. Nature (London) 227:680–685.
16. Leenhouts, K. and G. Venema. 1992. Molecular cloning and expression in Lactococcus. Med. Fac. Landbouww. Univ. Gent. 57:2031–2043.
17. Longchamp, P. F., C. Mauel, and D. Karamata. 1994. Lytic enzymes associated with defective prophages of Bacillus subtilis: sequencing and characterization of the region comprising the N-acetylmuramoyl-L-alanine amidase gene of prophage PBSX. Microbiol. 140:1855–1867.
18. López, R., E. García, P. García, and J. L. García. 1995. Architecture and domain interchange of the pneumococcal cell wall lytic enzymes. Dev. Biol. Stand. 85:273–281.
19. Oda, Y., R. Nakayama, A. Kuroda, and J. Sekiguchi. 1993. Molecular cloning, sequence analysis, and characterization of a new cell wall hydrolase, CwlL, of Bacillus licheniformis. Mol. Gen. Genet. 241:380–388.
20. Oshida, T., M. Sugai, H. Komatsuzawa, Y. M. Hong, H. Suginaka, and A. Tomasz. 1995. A Staphylococcus aureus autolysin that has an N-acetylmuramoyl-L-alanine amidase domain and an endo-b-N-acetylglucosaminidase domain: Cloning, sequence analysis, and characterization. Proc. Natl. Acad. Sci. USA 92:285–289.
21. Pérez Martínez, G., J. Kok, G. Venema, J. M. van Dijl, H. Smith, and S. Bron. 1992. Protein export elements from Lactococcus lactis. Mol. Gen. Genet. 234:401–411.
22. Potvin, C., D. Leclerc, G. Tremblay, A. Asselin, and G. Bellemare. 1988. Cloning, sequencing and expression of a Bacillus bacteriolytic enzyme in Escherichia coli. Mol. Gen. Genet. 214:241–248.
23. Rashid, M. H., M. Mori, and J. Sekiguchi. 1995. Glucosaminidase of Bacillus subtilis: Cloning, regulation, primary structure and biochemical characterization. Microbiol. 141:2391–2404.
24. Ruhland, G. J., M. Hellwig, G. Wanner, and F. Feidler. 1993. Cell-surface location of Listeria-specific protein p60: detection of Listeria cells by indirect immunofluorescence. J. Gen. Microbiol. 139:609–616.
25. Sambrook, J., E. F. Fritsch, and T. Maniatis. 1989. Molecular cloning: a laboratory manual. Cold Spring Harbor Laboratory Press, Cold Spring Harbor, N.-Y.

26. Sanger, F., S. Nicklen, and A. R. Coulson. 1977. DNA sequencing with chain-terminating inhibitors. Proc. Natl. Acad. Sci. USA 74:5463–5467.
27. Sanz, J. M., P. Garcia, and J. L. Garcia. 1996. Construction of a multifunctional pneumococcal murein hydrolase by module assembly. Eur. J. Biochem. 235:601–605.
28. Sheehan, M. M., J. L. García, R. López, and P. García. 1996. Analysis of the catalytic domain of the lysin of the lactococcal bacteriophage Tuc2009 by chimeric gene assembling. FEMS Microbiol. Lett. 140:23–28.
29. Smith, H., S. Bron, J. van Ee, and G. Venema. 1987. Construction and use of signal sequence selection vectors in *Escherichia coli* and *Bacillus subtilis*. J. Bacteriol. 169:3321–3328.
30. Studier, F. W. and B. A. Moffatt. 1986. Use of bacteriophage T7 RNA polymerase to direct selective high-level expression of cloned genes. J. Mol. Biol. 189: 113–130.
31. Towbin, H., T. Staechelin, and J. Gordon. 1979. Electrophoretic transfer of proteins from polyacrylamide gels to nitrocellulose sheets: procedure and some applications. Proc. Natl. Acad. Sci. USA 76:4350–4354.
32. van De Guchte, M., J. Kodde, J. M. B. van der Vossen, J. Kok, and G. Venema. 1990. Heterologous gene expression in *Lactococcus lactis* ssp. lactis: Synthesis, secretion, and processing of the *Bacillus subtilis* neutral protease. Appl. Environ. Microbiol. 56:2606–2611.
33. van Dijl, J. M., A. de Jong, J. Vehmaanpera, G. Venema, and S. Bron. 1992. Signal peptidase I of *Bacillus subtilis*: patterns of conserved amino acids in prokaryotic and eukaryotic type I signal peptidases. EMBO J. 11:2819–2828.
34. Vasala, A., M. Valkkila, J. Caldentey, and T. Alatossava. 1995. Genetic and biochemical characterization of the *Lactobacillus delbrueckii* subsp. *lactis* bacteriophage LL-H lysin. Appl. Environ. Microbiol. 61:4004–4011.
35. Vieira, J. and J. Messing. 1991. New pUC-derived cloning vectors with different selectable markers and DNA replication origins. Gene 100:189–194.
36. Wilson, R., R. Ainscough, K. Anderson, C. Baynes, M. Berks, J. Bonfield, J. Burton, M. Connell, T. Copsey, J. Cooper, and et al. 1994. 2.2 Mb of contiguous nucleotide sequence from chromosome III of *C. elegans*. Nature 368:32–38.
37. Zabarovsky, E. R. and G. Winberg. 1990. High efficiency electroporation of ligated DNA into bacteria. Nucl. Acid Res. 18:5912.
38. Stahl and Uhlen, TIBTECH May 1997, 15, 185–192
39. WO 94/18830
40. WO 97/08553
41. Medaglini et al., PNAS 1995, 2; 6868–6872
42. Robinson et al., Nature Biotechnology 1997, 15; 653–657

The invention claimed is:

1. A method for attaching a substance to the cell wall of a microorganism, said method comprising:

attaching the substance to a cell wall of the microorganism with an attaching peptide comprising at least one AcmA repeat comprising SEQ ID NO:17, wherein the AcmA repeat is capable of attaching the substance to the cell wall of the microorganism.

2. The method according to claim 1, wherein the attaching peptide originates from the major peptidoglycan hydrolase of *Lactococcus lactis*.

3. The method according to claim 1, further comprising: wherein attaching the substance to the cell wall of the microorganism comprises attaching an antigenic substance to the cell wall of the microorganism; and formulating said microorganism with suitable pharmaceutical excipients, thus producing a vaccine.

4. The method according to claim 1 further comprising: wherein attaching the substance to the cell wall of the microorganism comprises attaching an antigenic substance to the cell wall of the microorganism; formulating said microorganism with suitable pharmaceutical excipients to form a formulation; and injecting a subject with said formulation.

5. In a method for attaching a heterologous peptide to a recombinant microorganism's outer surface, an improvement comprising:

using a peptide comprising at least one AcmA repeat to attach the heterologous peptide to the outer surface of the recombinant microorganism, wherein, structurally, the at least one AcmA repeat comprises SEQ ID NO:17, and wherein, functionally, the at least one AcmA repeat is able to attach a substance to a cell wall of a microorganism.

6. A process for anchoring a substance to a microorganism's cell wall, said process comprising:

attaching a substance to an AcmA means for binding to the cell wall of the microorganism, wherein said AcmA means for binding to the cell wall of the microorganism comprises the amino acid sequence of SEQ ID NO:17; and placing the AcmA means for binding to the cell wall of the microorganism attached to the substance in contact with a microorganism so that the AcmA means for binding to the cell wall of the microorganism anchors to the microorganism's cell wall.

7. The method according to claim 1, wherein the microorganism is a non-recombinant microorganism.

8. The method according to claim 3, wherein the microorganism is a non-recombinant microorganism.

9. The method according to claim 4, wherein the microorganism is a non-recombinant microorganism.

10. The method according to claim 1, wherein the substance is selected from the group consisting of an antigenic determinant, an enzyme, an antibody, a single-chain antibody, a fragment of an antibody, a fragment of a single chain antibody, a polyhistidyl tag, a fluorescing protein, luciferase, a binding peptide, an antibiotic, a hormone, a non-peptide antigenic determinant, a carbohydrate, a fatty acid, an aromatic compound, and a reporter molecule.

11. The method according to claim 3, further comprising injecting a subject with the vaccine that was produced.

* * * * *

UNITED STATES PATENT AND TRADEMARK OFFICE
CERTIFICATE OF CORRECTION

PATENT NO. : 7,169,383 B1 Page 1 of 1
APPLICATION NO. : 09/554354
DATED : January 30, 2007
INVENTOR(S) : Girbe Buist et al.

It is certified that error appears in the above-identified patent and that said Letters Patent is hereby corrected as shown below:

In the specification:

| | | |
|---|---|---|
| COLUMN 10, | LINES 28,29, | change "glucosamimidase" to --glucosaminidase-- |
| COLUMN 10, | LINE 30, | change "glucosamimidase" to --glucosaminidase-- |
| COLUMN 12, | LINE 31, | change "4, and ~3," to --4, and 3,-- |
| COLUMN 19, | LINE 24, | change "L. *lactisconsists*" to --L. *lactis* consists-- |
| COLUMN 25, | LINE 44, | change "*lysodeikticus*autoclaved" to --*lysodeikticus* autoclaved-- |

Signed and Sealed this

Twenty-third Day of December, 2008

JON W. DUDAS
*Director of the United States Patent and Trademark Office*

```
                       SEQUENCE LISTING

<160> NUMBER OF SEQ ID NOS: 110

<210> SEQ ID NO 1
<211> LENGTH: 27
<212> TYPE: DNA
<213> ORGANISM: Artificial Sequence
<220> FEATURE:
<223> OTHER INFORMATION: Description of Artificial Sequence:
      oligonucleotide REPDEL-1

<400> SEQUENCE: 1
cgcgaattca gattatgaaa caataag                                      27

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence:
      oligonucleotide REPDEL-2

<400> SEQUENCE: 2
cgcgaattct tatgtcagta caagttttg                                    30

<210> SEQ ID NO 3
<211> LENGTH: 28
<212> TYPE: DNA
<213> ORGANISM: Artificial Sequence
<220> FEATURE:
<223> OTHER INFORMATION: Description of Artificial Sequence:
      oligonucleotide REPDEL-3

<400> SEQUENCE: 3
cgcgaattcc ttatgaagaa gctccgtc                                     28
```

```
<210> SEQ ID NO 4
<211> LENGTH: 17
<212> TYPE: DNA
<213> ORGANISM: Artificial Sequence
<220> FEATURE:
<223> OTHER INFORMATION: Description of Artificial Sequence:
      oligonucleotide ALA-4

<400> SEQUENCE: 4
cttcaacaga caagtcc                                                   17

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence:
      oligonucleotide REP-4A

<400> SEQUENCE: 5
agcaatacta gttttata                                                  18

<210> SEQ ID NO 6
<211> LENGTH: 36
<212> TYPE: DNA
<213> ORGANISM: Artificial Sequence
<220> FEATURE:
<223> OTHER INFORMATION: Description of Artificial Sequence:
      oligonucleotide REP-4B

<400> SEQUENCE: 6
cgcgaattcg ctagcgtcgc tcaaattcaa agtgcg                              36

<210> SEQ ID NO 7
<211> LENGTH: 28
<212> TYPE: DNA
<213> ORGANISM: Artificial Sequence
<220> FEATURE:
<223> OTHER INFORMATION: Description of Artificial Sequence:
      oligonucleotide ACMHIS

<400> SEQUENCE: 7
aggagatctg cgactaactc atcagagg                                       28

<210> SEQ ID NO 8
<211> LENGTH: 17
<212> TYPE: DNA
<213> ORGANISM: Artificial Sequence
<220> FEATURE:
<223> OTHER INFORMATION: Description of Artificial Sequence:
      oligonucleotide BETA-1

<400> SEQUENCE: 8
ggatcatgta actcgcc                                                   17

<210> SEQ ID NO 9
<211> LENGTH: 26
<212> TYPE: DNA
<213> ORGANISM: Artificial Sequence
<220> FEATURE:
<223> OTHER INFORMATION: Description of Artificial Sequence:
      oligonucleotide BETA-2

<400> SEQUENCE: 9
ggaatccata tgcttaatca gtgagg                                         26

<210> SEQ ID NO 10
```

-continued

```
<211> LENGTH: 17
<212> TYPE: DNA
<213> ORGANISM: Artificial Sequence
<220> FEATURE:
<223> OTHER INFORMATION: Description of Artificial Sequence:
      oligonucleotide ALFA-A

<400> SEQUENCE: 10
gcatccgttg aaagcgg                                                   17

<210> SEQ ID NO 11
<211> LENGTH: 27
<212> TYPE: DNA
<213> ORGANISM: Artificial Sequence
<220> FEATURE:
<223> OTHER INFORMATION: Description of Artificial Sequence:
      oligonucleotide ALFA-B

<400> SEQUENCE: 11
gaattcgata tctttgaaca taaattg                                        27

<210> SEQ ID NO 12
<211> LENGTH: 18
<212> TYPE: DNA
<213> ORGANISM: Artificial Sequence
<220> FEATURE:
<223> OTHER INFORMATION: Description of Artificial Sequence:
      oligonucleotide ALA-14

<400> SEQUENCE: 12
gataaaatga ttccaagc                                                  18

<210> SEQ ID NO 13
<211> LENGTH: 17
<212> TYPE: DNA
<213> ORGANISM: Artificial Sequence
<220> FEATURE:
<223> OTHER INFORMATION: Description of Artificial Sequence:
      oligonucleotide ALA-22

<400> SEQUENCE: 13
ctcaaattca aagtgcg                                                   17

<210> SEQ ID NO 14
<211> LENGTH: 45
<212> TYPE: PRT
<213> ORGANISM: Lactococcus lactis
<220> FEATURE:
<223> OTHER INFORMATION: /note="repeat 1 of the genome lactococcus
      lactis"

<400> SEQUENCE: 14

Thr Thr Tyr Thr Val Lys Ser Gly Asp Thr Leu Trp Gly Ile Ser Gln
  1               5                  10                  15

Arg Tyr Gly Ile Ser Val Ala Gln Ile Gln Ser Ala Asn Asn Leu Lys
             20                  25                  30

Ser Thr Ile Ile Tyr Ile Gly Gln Lys Leu Val Leu Thr
         35                  40                  45

<210> SEQ ID NO 15
<211> LENGTH: 45
<212> TYPE: PRT
<213> ORGANISM: Lactococcus lactis
<220> FEATURE:
<223> OTHER INFORMATION: /note="repeat 2 of the genome lactococcus
      lactis"
```

-continued

```
<400> SEQUENCE: 15

Thr Thr Val Lys Val Lys Ser Gly Asp Thr Leu Trp Ala Leu Ser Val
1               5                   10                  15

Lys Tyr Lys Thr Ser Ile Ala Gln Leu Lys Ser Trp Asn His Leu Ser
                20                  25                  30

Ser Asp Thr Ile Tyr Ile Gly Gln Asn Leu Ile Val Ser
                35                  40                  45

<210> SEQ ID NO 16
<211> LENGTH: 45
<212> TYPE: PRT
<213> ORGANISM: Lactococcus lactis
<220> FEATURE:
<223> OTHER INFORMATION: /note="repeat 3 of the genome lactococcus
      lactis"

<400> SEQUENCE: 16

Ser Ile His Lys Val Lys Gly Asp Thr Leu Trp Gly Leu Ser Gln
1               5                   10                  15

Lys Ser Gly Ser Pro Ile Ala Ser Ile Lys Ala Trp Asn His Leu Ser
                20                  25                  30

Ser Asp Thr Ile Leu Ile Gly Gln Tyr Leu Arg Ile Lys
                35                  40                  45

<210> SEQ ID NO 17
<211> LENGTH: 45
<212> TYPE: PRT
<213> ORGANISM: Lactococcus lactis
<220> FEATURE:
<221> NAME/KEY: SITE
<222> LOCATION: (2)..(45)
<223> OTHER INFORMATION: /note=""Xaa" on pos. 2, 5, 10, 11, 14-22,
      24-26, 28, 29, 31-35, 37, 38, 41, 43, 45 stands for any amino
      acid"
<220> FEATURE:
<221> NAME/KEY: SITE
<222> LOCATION: (1)..(44)
<223> OTHER INFORMATION: / note="Xaa" on pos. 1 stands for Tyr or His
<223> OTHER INFORMATION: / note="Xaa" on pos. 3 stands for Val, Ile or
      Leu
<223> OTHER INFORMATION: / note="Xaa" on pos. 4 stands for Lys or Arg
<223> OTHER INFORMATION: / note="Xaa" on pos. 7 stands for Asp or Glu
<223> OTHER INFORMATION: / note="Xaa" on pos. 8 stands for Thr or Ser
<223> OTHER INFORMATION: / note="Xaa" on pos. 9 stands for Leu, Val or
      Ile
<223> OTHER INFORMATION: / note="Xaa" on pos. 12 stands for Ile, Leu or
      Val
<223> OTHER INFORMATION: / note="Xaa" on pos. 13 stands for Ala or Ser
<223> OTHER INFORMATION: / note="Xaa" on pos. 23 stands for Leu or Ile
<223> OTHER INFORMATION: / note="Xaa" on pos. 30 stands for Leu or Ile
<223> OTHER INFORMATION: / note="Xaa" on pos. 36 stands for Ile, Leu or
      Val
<223> OTHER INFORMATION: / note="Xaa" on pos. 42 stands for Ile, Leu or
      Val
<223> OTHER INFORMATION: / note="Xaa" on pos. 44 stands for Val, Ile or
      Leu"

<400> SEQUENCE: 17

Xaa Xaa Xaa Xaa Xaa Gly Xaa Xaa Xaa Xaa Xaa Xaa Xaa Xaa Xaa
1               5                   10                  15

Xaa Xaa Xaa Xaa Xaa Xaa Xaa Xaa Xaa Xaa Asn Xaa Xaa Xaa Xaa Xaa
                20                  25                  30

Xaa Xaa Xaa Xaa Xaa Xaa Gly Gln Xaa Xaa Xaa Xaa Xaa
                35                  40                  45

<210> SEQ ID NO 18
```

```
<400> SEQUENCE: 18

000

<210> SEQ ID NO 19

<400> SEQUENCE: 19

000

<210> SEQ ID NO 20
<211> LENGTH: 43
<212> TYPE: PRT
<213> ORGANISM: Lactococcus lactis

<400> SEQUENCE: 20

Tyr Thr Val Lys Ser Gly Asp Thr Leu Trp Gly Ile Ser Gln Arg Tyr
 1               5                  10                  15

Gly Ile Ser Val Ala Gln Ile Gln Ser Ala Asn Asn Leu Lys Ser Thr
            20                  25                  30

Ile Ile Tyr Ile Gly Gln Lys Leu Val Leu Thr
        35                  40

<210> SEQ ID NO 21
<211> LENGTH: 43
<212> TYPE: PRT
<213> ORGANISM: Lactococcus lactis

<400> SEQUENCE: 21

Val Lys Val Lys Ser Gly Asp Thr Leu Trp Ala Leu Ser Val Lys Tyr
 1               5                  10                  15

Lys Thr Ser Ile Ala Gln Leu Lys Ser Trp Asn His Leu Ser Ser Asp
            20                  25                  30

Thr Ile Tyr Ile Gly Gln Asn Leu Ile Val Ser
        35                  40

<210> SEQ ID NO 22
<211> LENGTH: 43
<212> TYPE: PRT
<213> ORGANISM: Lactococcus lactis

<400> SEQUENCE: 22

His Lys Val Val Lys Gly Asp Thr Leu Trp Gly Leu Ser Val Lys Ser
 1               5                  10                  15

Gly Ser Pro Ile Ala Ser Ile Lys Ala Trp Asn His Leu Ser Ser Asp
            20                  25                  30

Thr Ile Leu Ile Gly Gln Tyr Leu Arg Ile Lys
        35                  40

<210> SEQ ID NO 23
<211> LENGTH: 43
<212> TYPE: PRT
<213> ORGANISM: Enterococcus faecalis

<400> SEQUENCE: 23

Tyr Thr Val Lys Ser Gly Asp Thr Leu Asn Lys Ile Ala Ala Gln Tyr
 1               5                  10                  15

Gly Val Ser Val Ala Asn Leu Arg Ser Trp Asn Gly Ile Ser Gly Asp
            20                  25                  30

Leu Ile Phe Val Gly Gln Lys Leu Ile Val Lys
        35                  40
```

<210> SEQ ID NO 24
<211> LENGTH: 43
<212> TYPE: PRT
<213> ORGANISM: Enterococcus faecalis

<400> SEQUENCE: 24

Tyr Thr Val Lys Ser Gly Asp Thr Leu Asn Lys Ile Ala Ala Gln Tyr
1               5                   10                  15

Gly Val Thr Val Ala Asn Leu Arg Ser Trp Asn Gly Ile Ser Gly Asp
            20                  25                  30

Leu Ile Phe Val Gly Gln Lys Leu Ile Val Lys
        35                  40

<210> SEQ ID NO 25
<211> LENGTH: 43
<212> TYPE: PRT
<213> ORGANISM: Enterococcus faecalis

<400> SEQUENCE: 25

Tyr Thr Ile Lys Ser Gly Asp Thr Leu Asn Lys Ile Ala Ala Gln Tyr
1               5                   10                  15

Gly Val Ser Val Ala Asn Leu Arg Ser Trp Asn Gly Ile Ser Gly Asp
            20                  25                  30

Leu Ile Phe Ala Gly Gln Lys Ile Ile Val Lys
        35                  40

<210> SEQ ID NO 26
<211> LENGTH: 43
<212> TYPE: PRT
<213> ORGANISM: Enterococcus faecalis

<400> SEQUENCE: 26

Tyr Thr Ile Lys Ser Gly Asp Thr Leu Asn Lys Ile Ser Ala Gln Phe
1               5                   10                  15

Gly Val Ser Val Ala Asn Leu Arg Ser Trp Asn Gly Ile Lys Gly Asp
            20                  25                  30

Leu Ile Phe Ala Gly Gln Thr Ile Ile Val Lys
        35                  40

<210> SEQ ID NO 27
<211> LENGTH: 43
<212> TYPE: PRT
<213> ORGANISM: Enterococcus faecalis

<400> SEQUENCE: 27

His Thr Val Lys Ser Gly Asp Ser Leu Trp Gly Leu Ser Met Gln Tyr
1               5                   10                  15

Gly Ile Ser Ile Gln Lys Ile Lys Gln Leu Asn Gly Leu Ser Gly Asp
            20                  25                  30

Thr Ile Tyr Ile Gly Gln Thr Leu Lys Val Gly
        35                  40

<210> SEQ ID NO 28
<211> LENGTH: 43
<212> TYPE: PRT
<213> ORGANISM: Enterococcus hirae

<400> SEQUENCE: 28

Tyr Thr Val Lys Ser Gly Asp Ser Val Trp Gly Ile Ser His Ser Phe
1               5                   10                  15

Gly Ile Thr Met Ala Gln Leu Ile Glu Trp Asn Asn Ile Lys Asn Asn
            20                  25                  30

Phe Ile Tyr Pro Gly Gln Lys Leu Thr Ile Lys
        35                  40

<210> SEQ ID NO 29
<211> LENGTH: 43
<212> TYPE: PRT
<213> ORGANISM: Enterococcus hirae

<400> SEQUENCE: 29

Tyr Thr Val Lys Ser Gly Asp Ser Val Trp Lys Ile Ala Asn Asp His
 1               5                  10                  15

Gly Ile Ser Met Asn Gln Leu Ile Glu Trp Asn Asn Ile Lys Asn Asn
            20                  25                  30

Phe Val Tyr Pro Gly Gln Gln Leu Val Val Ser
        35                  40

<210> SEQ ID NO 30
<211> LENGTH: 43
<212> TYPE: PRT
<213> ORGANISM: Enterococcus hirae

<400> SEQUENCE: 30

Tyr Thr Val Lys Ala Gly Glu Ser Val Trp Ser Val Ser Asn Lys Phe
 1               5                  10                  15

Gly Ile Ser Met Asn Gln Leu Ile Gln Trp Asn Asn Ile Lys Asn Asn
            20                  25                  30

Phe Ile Tyr Pro Gly Gln Lys Leu Ile Val Lys
        35                  40

<210> SEQ ID NO 31
<211> LENGTH: 43
<212> TYPE: PRT
<213> ORGANISM: Enterococcus hirae

<400> SEQUENCE: 31

Tyr Thr Val Lys Ala Gly Glu Ser Val Trp Gly Val Ala Asn Lys Asn
 1               5                  10                  15

Gly Ile Ser Met Asn Gln Leu Ile Glu Trp Asn Asn Ile Lys Asn Asn
            20                  25                  30

Phe Ile Tyr Pro Gly Gln Lys Leu Ile Val Lys
        35                  40

<210> SEQ ID NO 32
<211> LENGTH: 43
<212> TYPE: PRT
<213> ORGANISM: Enterococcus hirae

<400> SEQUENCE: 32

Tyr Thr Val Lys Ala Gly Glu Ser Val Trp Gly Val Ala Asn Lys His
 1               5                  10                  15

His Ile Thr Met Asp Gln Leu Ile Glu Trp Asn Asn Ile Lys Asn Asn
            20                  25                  30

Phe Ile Tyr Pro Gly Glu Val Ile Val Lys
        35                  40

<210> SEQ ID NO 33
<211> LENGTH: 43
<212> TYPE: PRT
<213> ORGANISM: Enterococcus hirae

<400> SEQUENCE: 33

Tyr Thr Val Lys Ala Gly Glu Ser Val Trp Gly Val Ala Asp Ser His
1               5                   10                  15

Gly Ile Thr Met Asn Gln Leu Ile Glu Trp Asn Asn Ile Lys Asn Asn
            20                  25                  30

Phe Ile Tyr Pro Gly Gln Gln Leu Ile Val Lys
        35                  40

<210> SEQ ID NO 34
<211> LENGTH: 44
<212> TYPE: PRT
<213> ORGANISM: Lactococcus sp.

<400> SEQUENCE: 34

Tyr Val Val Lys Gln Gly Asp Thr Leu Ser Gly Ile Ala Ser Asn Trp
1               5                   10                  15

Gly Thr Asn Trp Gln Glu Leu Ala Arg Gln Asn Ser Leu Ser Asn Pro
            20                  25                  30

Asn Met Ile Tyr Ala Gly Gln Val Ile Ser Phe Thr
        35                  40

<210> SEQ ID NO 35
<211> LENGTH: 43
<212> TYPE: PRT
<213> ORGANISM: Lactococcus sp.

<400> SEQUENCE: 35

Tyr Thr Val Gln Ser Gly Asp Asn Leu Ser Ser Ile Ala Ile Leu Leu
1               5                   10                  15

Gly Thr Thr Val Gln Ser Leu Val Ser Met Asn Gly Ile Ser Asn Pro
            20                  25                  30

Asn Leu Ile Tyr Ala Gly Gln Thr Leu Asn Tyr
        35                  40

<210> SEQ ID NO 36
<211> LENGTH: 44
<212> TYPE: PRT
<213> ORGANISM: Lactococcus sp.

<400> SEQUENCE: 36

Tyr Ile Val Lys Gln Gly Asp Thr Leu Ser Gly Ile Ala Ser Asn Leu
1               5                   10                  15

Gly Thr Asn Trp Gln Glu Leu Ala Arg Gln Asn Ser Leu Ser Asn Pro
            20                  25                  30

Asn Met Ile Tyr Ser Gly Gln Val Ile Ser Leu Thr
        35                  40

<210> SEQ ID NO 37
<211> LENGTH: 43
<212> TYPE: PRT
<213> ORGANISM: Lactococcus sp.

<400> SEQUENCE: 37

Tyr Thr Val Gln Ser Gly Asp Asn Leu Ser Ser Ile Ala Arg Arg Leu
1               5                   10                  15

Gly Thr Thr Val Gln Ser Leu Val Ser Met Asn Gly Ile Ser Asn Pro
            20                  25                  30

Asn Leu Ile Tyr Ala Gly Gln Thr Leu Asn Tyr
        35                  40

<210> SEQ ID NO 38
<211> LENGTH: 44
<212> TYPE: PRT
<213> ORGANISM: Bacillus sp.

<400> SEQUENCE: 38

Tyr Val Val Lys Gln Gly Asp Thr Leu Thr Ser Ile Ala Arg Ala Phe
1               5                   10                  15

Gly Val Thr Val Ala Gln Leu Gln Glu Trp Asn Asn Ile Glu Asp Pro
            20                  25                  30

Asn Leu Ile Arg Val Gly Gln Val Leu Ile Val Ser
        35                  40

<210> SEQ ID NO 39
<211> LENGTH: 45
<212> TYPE: PRT
<213> ORGANISM: Bacillus sp.

<400> SEQUENCE: 39

Tyr Lys Val Lys Ser Gly Asp Asn Leu Thr Lys Ile Ala Lys Lys His
1               5                   10                  15

Asn Thr Thr Val Ala Thr Leu Leu Lys Leu Asn Pro Ser Ile Lys Asp
            20                  25                  30

Pro Asn Met Ile Arg Val Gly Gln Thr Ile Asn Val Thr
        35                  40                  45

<210> SEQ ID NO 40
<211> LENGTH: 45
<212> TYPE: PRT
<213> ORGANISM: Bacillus sp.

<400> SEQUENCE: 40

His Lys Val Lys Ser Gly Asp Thr Leu Ser Lys Ile Ala Val Asp Asn
1               5                   10                  15

Lys Thr Thr Val Ser Arg Leu Met Ser Leu Asn Pro Glu Ile Thr Asn
            20                  25                  30

Pro Asn His Ile Lys Val Gly Gln Thr Ile Arg Leu Ser
        35                  40                  45

<210> SEQ ID NO 41
<211> LENGTH: 45
<212> TYPE: PRT
<213> ORGANISM: Bacillus sp.

<400> SEQUENCE: 41

His Val Val Lys Lys Gly Asp Thr Leu Ser Glu Ile Ala Lys Lys Ile
1               5                   10                  15

Lys Thr Ser Thr Lys Thr Leu Leu Glu Leu Asn Pro Thr Ile Lys Asn
            20                  25                  30

Pro Asn Lys Ile Tyr Val Gly Gln Arg Ile Asn Val Gly
        35                  40                  45

<210> SEQ ID NO 42
<211> LENGTH: 44
<212> TYPE: PRT
<213> ORGANISM: Bacillus sp.

<400> SEQUENCE: 42

Tyr Thr Val Val Ser Gly Asp Ser Trp Trp Lys Ile Ala Gln Arg Asn
1               5                   10                  15

-continued

Gly Leu Ser Met Tyr Thr Leu Ala Ser Gln Asn Gly Lys Ser Ile Tyr
            20                  25                  30

Ser Thr Ile Tyr Pro Gly Asn Lys Leu Ile Ile Lys
            35                  40

<210> SEQ ID NO 43
<211> LENGTH: 44
<212> TYPE: PRT
<213> ORGANISM: Bacillus sp.

<400> SEQUENCE: 43

Tyr Thr Val Val Ser Gly Asp Ser Trp Trp Lys Ile Ala Gln Arg Asn
1               5                   10                  15

Gly Leu Ser Met Tyr Thr Leu Ala Ser Gln Asn Gly Lys Ser Ile Tyr
            20                  25                  30

Ser Thr Ile Tyr Pro Gly Asn Lys Leu Ile Ile Lys
            35                  40

<210> SEQ ID NO 44
<211> LENGTH: 44
<212> TYPE: PRT
<213> ORGANISM: Bacillus sphaericus

<400> SEQUENCE: 44

Ile Leu Ile Arg Pro Gly Asp Ser Leu Trp Tyr Phe Ser Asp Leu Phe
1               5                   10                  15

Lys Ile Pro Leu Gln Leu Leu Asp Ser Asn Arg Asn Ile Asn Pro
            20                  25                  30

Gln Leu Leu Gln Val Gly Gln Arg Ile Gln Ile Pro
            35                  40

<210> SEQ ID NO 45
<211> LENGTH: 44
<212> TYPE: PRT
<213> ORGANISM: Bacillus sphaericus

<400> SEQUENCE: 45

Tyr Thr Ile Thr Gln Gly Asp Ser Leu Trp Gln Ile Ala Gln Asn Lys
1               5                   10                  15

Asn Leu Pro Leu Asn Ala Ile Leu Leu Val Asn Pro Glu Ile Gln Pro
            20                  25                  30

Ser Arg Leu His Ile Gly Gln Thr Ile Gln Val Pro
            35                  40

<210> SEQ ID NO 46
<211> LENGTH: 43
<212> TYPE: PRT
<213> ORGANISM: Haemophilus influenzae

<400> SEQUENCE: 46

His Ile Val Lys Lys Gly Glu Ser Leu Gly Ser Leu Ser Asn Lys Tyr
1               5                   10                  15

His Val Lys Val Ser Asp Ile Ile Lys Leu Asn Gln Leu Lys Arg Lys
            20                  25                  30

Thr Leu Trp Leu Asn Glu Ser Ile Lys Ile Pro
            35                  40

<210> SEQ ID NO 47
<211> LENGTH: 45
<212> TYPE: PRT

-continued

<213> ORGANISM: Haemophilus influenzae

<400> SEQUENCE: 47

His Lys Val Thr Asn Lys Asn Gln Thr Leu Tyr Ala Ile Ser Arg Glu
1               5                   10                  15

Tyr Asn Ile Pro Val Asn Ile Leu Ser Leu Asn Pro His Leu Lys
            20                  25                  30

Asn Gly Lys Val Ile Thr Gly Gln Lys Ile Lys Leu Arg
        35                  40                  45

<210> SEQ ID NO 48
<211> LENGTH: 43
<212> TYPE: PRT
<213> ORGANISM: Listeria monocytogenes

<400> SEQUENCE: 48

Val Val Val Glu Ala Gly Asp Thr Leu Trp Gly Ile Ala Gln Ser Lys
1               5                   10                  15

Gly Thr Thr Val Asp Ala Ile Lys Lys Ala Asn Asn Leu Thr Thr Asp
            20                  25                  30

Lys Ile Val Pro Gly Gln Lys Leu Gln Val Asn
        35                  40

<210> SEQ ID NO 49
<211> LENGTH: 43
<212> TYPE: PRT
<213> ORGANISM: Listeria monocytogenes

<400> SEQUENCE: 49

His Ala Val Lys Ser Gly Asp Thr Ile Trp Ala Leu Ser Val Lys Tyr
1               5                   10                  15

Gly Val Ser Val Gln Asp Ile Met Ser Trp Asn Asn Leu Ser Ser Ser
            20                  25                  30

Ser Ile Tyr Val Gly Gln Lys Leu Ala Ile Lys
        35                  40

<210> SEQ ID NO 50
<211> LENGTH: 43
<212> TYPE: PRT
<213> ORGANISM: Listeria innocua

<400> SEQUENCE: 50

Val Val Val Glu Ala Gly Asp Thr Leu Trp Gly Ile Ala Gln Ser Lys
1               5                   10                  15

Gly Thr Thr Val Asp Ala Ile Lys Lys Ala Asn Asn Leu Thr Thr Asp
            20                  25                  30

Lys Ile Val Pro Gly Gln Lys Leu Gln Val Asn
        35                  40

<210> SEQ ID NO 51
<211> LENGTH: 43
<212> TYPE: PRT
<213> ORGANISM: Listeria innocua

<400> SEQUENCE: 51

His Asn Val Lys Ser Gly Asp Thr Ile Trp Ala Leu Ser Val Lys Tyr
1               5                   10                  15

Gly Val Ser Val Gln Asp Ile Met Ser Trp Asn Asn Leu Ser Ser Ser
            20                  25                  30

Ser Ile Tyr Val Gly Gln Lys Pro Ala Ile Lys

-continued

<210> SEQ ID NO 52
<211> LENGTH: 43
<212> TYPE: PRT
<213> ORGANISM: Listeria ivanovii

<400> SEQUENCE: 52

Val Val Val Glu Ala Gly Asp Thr Leu Trp Gly Ile Ala Gln Asp Lys
1               5                   10                  15

Gly Thr Thr Val Asp Ala Leu Lys Lys Ala Asn Asn Leu Thr Ser Asp
            20                  25                  30

Lys Ile Val Pro Gly Gln Lys Leu Gln Ile Thr
        35                  40

<210> SEQ ID NO 53
<211> LENGTH: 43
<212> TYPE: PRT
<213> ORGANISM: Listeria ivanovii

<400> SEQUENCE: 53

Tyr Thr Val Lys Ser Gly Asp Thr Ile Trp Ala Leu Ser Ser Lys Tyr
1               5                   10                  15

Gly Thr Ser Val Gln Asn Ile Met Ser Trp Asn Asn Leu Ser Ser Ser
            20                  25                  30

Ser Ile Tyr Val Gly Gln Val Leu Ala Val Lys
        35                  40

<210> SEQ ID NO 54
<211> LENGTH: 43
<212> TYPE: PRT
<213> ORGANISM: Listeria ivanovii

<400> SEQUENCE: 54

Tyr Thr Val Lys Ser Gly Asp Thr Leu Ser Lys Ile Ala Thr Thr Phe
1               5                   10                  15

Gly Thr Thr Val Ser Lys Ile Lys Ala Leu Asn Gly Leu Asn Ser Asp
            20                  25                  30

Asn Leu Gln Val Gly Gln Val Leu Lys Val Lys
        35                  40

<210> SEQ ID NO 55
<211> LENGTH: 43
<212> TYPE: PRT
<213> ORGANISM: Listeria seeligeri

<400> SEQUENCE: 55

Val Val Val Glu Ala Gly Asp Thr Leu Trp Gly Ile Ala Gln Asp Asn
1               5                   10                  15

Gly Thr Thr Val Asp Ala Leu Lys Lys Ala Asn Lys Leu Thr Thr Asp
            20                  25                  30

Lys Ile Val Pro Gly Gln Lys Leu Gln Val Thr
        35                  40

<210> SEQ ID NO 56
<211> LENGTH: 43
<212> TYPE: PRT
<213> ORGANISM: Listeria seeligeri

<400> SEQUENCE: 56

His Thr Val Lys Ser Gly Asp Thr Ile Trp Ala Leu Ser Val Lys Tyr

-continued

```
                1               5                  10                  15
Gly Ala Ser Val Gln Asp Leu Met Ser Trp Asn Asn Leu Ser Ser Ser
                        20                  25                  30

Ser Ile Tyr Val Gly Gln Asn Ile Ala Val Lys
                35                  40

<210> SEQ ID NO 57
<211> LENGTH: 43
<212> TYPE: PRT
<213> ORGANISM: Listeria seeligeri

<400> SEQUENCE: 57

Tyr Thr Val Lys Ser Gly Asp Thr Leu Gly Lys Ile Ala Ser Thr Phe
  1               5                  10                  15

Gly Thr Thr Val Ser Lys Ile Lys Ala Leu Asn Gly Leu Thr Ser Asp
                20                  25                  30

Asn Leu Gln Val Gly Asp Val Leu Lys Val Lys
                35                  40

<210> SEQ ID NO 58
<211> LENGTH: 43
<212> TYPE: PRT
<213> ORGANISM: Listeria welshimeri

<400> SEQUENCE: 58

Val Val Val Glu Ala Gly Asp Thr Leu Trp Gly Ile Ala Gln Ser Lys
  1               5                  10                  15

Gly Thr Thr Val Asp Ala Leu Lys Lys Ala Asn Asn Leu Thr Ser Asp
                20                  25                  30

Lys Ile Val Pro Gly Gln Lys Leu Gln Val Thr
                35                  40

<210> SEQ ID NO 59
<211> LENGTH: 43
<212> TYPE: PRT
<213> ORGANISM: Listeria welshimeri

<400> SEQUENCE: 59

His Thr Val Lys Ser Gly Asp Thr Ile Trp Ala Leu Ser Val Lys Tyr
  1               5                  10                  15

Gly Ala Ser Val Gln Asp Leu Met Ser Trp Asn Asn Leu Ser Ser Ser
                20                  25                  30

Ser Ile Tyr Val Gly Gln Lys Ile Ala Val Lys
                35                  40

<210> SEQ ID NO 60
<211> LENGTH: 43
<212> TYPE: PRT
<213> ORGANISM: Listeria welshimeri

<400> SEQUENCE: 60

Tyr Thr Val Lys Ser Gly Asp Ser Leu Ser Lys Ile Ala Asn Thr Phe
  1               5                  10                  15

Gly Thr Ser Val Ser Lys Ile Lys Ala Leu Asn Asn Leu Thr Ser Asp
                20                  25                  30

Asn Leu Gln Val Gly Thr Val Leu Lys Val Lys
                35                  40

<210> SEQ ID NO 61
<211> LENGTH: 43
```

```
<212> TYPE: PRT
<213> ORGANISM: Listeria grayi

<400> SEQUENCE: 61

Val Val Val Ala Ser Gly Asp Thr Leu Trp Gly Ile Ala Ser Lys Thr
 1               5                  10                  15

Gly Thr Thr Val Asp Gln Leu Lys Gln Leu Asn Lys Leu Asp Ser Asp
                20                  25                  30

Arg Ile Val Pro Gly Gln Lys Leu Thr Ile Lys
         35                  40

<210> SEQ ID NO 62
<211> LENGTH: 43
<212> TYPE: PRT
<213> ORGANISM: Listeria grayi

<400> SEQUENCE: 62

Tyr Lys Val Lys Ser Gly Asp Thr Ile Trp Ala Leu Ser Val Lys Tyr
 1               5                  10                  15

Gly Val Pro Val Gln Lys Leu Ile Glu Trp Asn Asn Leu Ser Ser Ser
                20                  25                  30

Ser Ile Tyr Val Gly Gln Thr Ile Ala Val Lys
         35                  40

<210> SEQ ID NO 63
<211> LENGTH: 44
<212> TYPE: PRT
<213> ORGANISM: Listeria grayi

<400> SEQUENCE: 63

Tyr Lys Val Gln Asn Gly Asp Ser Leu Gly Lys Ile Ala Ser Leu Phe
 1               5                  10                  15

Lys Val Ser Val Ala Asp Leu Thr Asn Trp Asn Asn Leu Asn Ala Thr
                20                  25                  30

Ile Thr Ile Tyr Ala Gly Gln Glu Leu Ser Val Lys
         35                  40

<210> SEQ ID NO 64
<211> LENGTH: 45
<212> TYPE: PRT
<213> ORGANISM: Escherichia coli

<400> SEQUENCE: 64

Tyr Val Val Ser Thr Gly Asp Thr Leu Ser Ser Ile Leu Asn Gln Tyr
 1               5                  10                  15

Gly Ile Asp Met Gly Asp Ile Ser Gln Leu Ala Ala Ala Asp Lys Glu
                20                  25                  30

Leu Arg Asn Leu Lys Ile Gly Gln Gln Leu Ser Trp Thr
         35                  40                  45

<210> SEQ ID NO 65
<211> LENGTH: 45
<212> TYPE: PRT
<213> ORGANISM: Haemophilus influenzae

<400> SEQUENCE: 65

Tyr Thr Val Thr Glu Gly Asp Thr Leu Lys Asp Val Leu Val Leu Ser
 1               5                  10                  15

Gly Leu Asp Asp Ser Ser Val Gln Pro Leu Ile Ala Leu Asp Pro Glu
                20                  25                  30
```

Leu Ala His Leu Lys Ala Gly Gln Gln Phe Tyr Trp Ile
        35                  40                  45

<210> SEQ ID NO 66
<211> LENGTH: 44
<212> TYPE: PRT
<213> ORGANISM: Escherichia coli

<400> SEQUENCE: 66

Tyr Thr Val Lys Lys Gly Asp Thr Leu Phe Tyr Ile Ala Trp Ile Thr
1               5                   10                  15

Gly Asn Asp Phe Arg Asp Leu Ala Gln Arg Asn Asn Ile Gln Ala Pro
            20                  25                  30

Tyr Ala Leu Asn Val Gly Gln Thr Leu Gln Val Gly
        35                  40

<210> SEQ ID NO 67
<211> LENGTH: 45
<212> TYPE: PRT
<213> ORGANISM: Haemophilus influenzae

<400> SEQUENCE: 67

Tyr Lys Val Asn Lys Gly Asp Thr Met Phe Leu Ile Ala Tyr Leu Ala
1               5                   10                  15

Gly Ile Asp Val Lys Glu Leu Ala Ala Leu Asn Asn Leu Ser Glu Pro
            20                  25                  30

Asn Tyr Asn Leu Ser Leu Gly Gln Val Leu Lys Ile Ser
        35                  40                  45

<210> SEQ ID NO 68
<211> LENGTH: 44
<212> TYPE: PRT
<213> ORGANISM: Haemophilus somnus

<400> SEQUENCE: 68

Tyr Lys Val Arg Lys Gly Asp Thr Met Phe Leu Ile Ala Tyr Ile Ser
1               5                   10                  15

Gly Met Asp Ile Lys Glu Leu Ala Thr Leu Asn Asn Met Ser Glu Pro
            20                  25                  30

Tyr His Leu Ser Ile Gly Gln Val Leu Lys Ile Ala
        35                  40

<210> SEQ ID NO 69
<211> LENGTH: 44
<212> TYPE: PRT
<213> ORGANISM: Pseudomonas aeruginosa

<400> SEQUENCE: 69

Tyr Ile Val Arg Arg Gly Asp Thr Leu Tyr Ser Ile Ala Phe Arg Phe
1               5                   10                  15

Gly Trp Asp Trp Lys Ala Leu Ala Ala Arg Asn Gly Ile Ala Pro Pro
            20                  25                  30

Tyr Thr Ile Gln Val Gly Gln Ala Ile Gln Phe Gly
        35                  40

<210> SEQ ID NO 70
<211> LENGTH: 44
<212> TYPE: PRT
<213> ORGANISM: Synechocystis sp.

<400> SEQUENCE: 70

His Gln Val Lys Glu Gly Glu Ser Leu Trp Gln Ile Ser Gln Ala Phe
1               5                   10                  15

Gln Val Asp Ala Lys Ala Ile Ala Leu Ala Asn Ser Ile Ser Thr Asp
                20                  25                  30

Thr Glu Leu Gln Ala Gly Gln Val Leu Asn Ile Pro
            35                  40

<210> SEQ ID NO 71
<211> LENGTH: 44
<212> TYPE: PRT
<213> ORGANISM: Sinorhizobium meliloti

<400> SEQUENCE: 71

Ile Met Val Arg Gln Gly Asp Thr Val Thr Val Leu Ala Arg Arg Phe
1               5                   10                  15

Gly Val Pro Glu Lys Glu Ile Leu Lys Ala Asn Gly Leu Lys Ser Ala
                20                  25                  30

Ser Gln Val Glu Pro Gly Gln Arg Leu Val Ile Pro
            35                  40

<210> SEQ ID NO 72
<211> LENGTH: 43
<212> TYPE: PRT
<213> ORGANISM: Escherichia coli

<400> SEQUENCE: 72

Tyr Thr Val Arg Ser Gly Asp Thr Leu Ser Ser Ile Ala Ser Arg Leu
1               5                   10                  15

Gly Val Ser Thr Lys Asp Leu Gln Gln Trp Asn Lys Leu Arg Gly Ser
                20                  25                  30

Lys Leu Lys Pro Gly Gln Ser Leu Thr Ile Gly
            35                  40

<210> SEQ ID NO 73
<211> LENGTH: 42
<212> TYPE: PRT
<213> ORGANISM: Escherichia coli

<400> SEQUENCE: 73

Tyr Arg Val Arg Lys Gly Asp Thr Leu Ser Ser Ile Ala Lys Arg His
1               5                   10                  15

Gly Val Asn Ile Lys Asp Val Met Arg Trp Asn Ser Asp Thr Ala Asn
                20                  25                  30

Leu Gln Pro Gly Asp Lys Leu Thr Leu Phe
            35                  40

<210> SEQ ID NO 74
<211> LENGTH: 44
<212> TYPE: PRT
<213> ORGANISM: Staphylococcus aureus

<400> SEQUENCE: 74

His Val Val Lys Pro Gly Asp Thr Val Asn Asp Ile Ala Lys Ala Asn
1               5                   10                  15

Gly Thr Thr Ala Asp Lys Ile Ala Ala Asp Asn Lys Leu Ala Asp Lys
                20                  25                  30

Asn Met Ile Lys Pro Gly Gln Glu Leu Val Val Asp
            35                  40

<210> SEQ ID NO 75

```
<211> LENGTH: 43
<212> TYPE: PRT
<213> ORGANISM: Bacillus subtilis

<400> SEQUENCE: 75

Ile Lys Val Lys Lys Gly Asp Thr Leu Trp Asp Leu Ser Arg Lys Tyr
 1               5                  10                  15

Asp Thr Thr Ile Ser Lys Ile Lys Ser Glu Asn His Leu Arg Ser Asp
                20                  25                  30

Ile Ile Tyr Val Gly Gln Thr Leu Ser Ile Asn
                35                  40

<210> SEQ ID NO 76
<211> LENGTH: 43
<212> TYPE: PRT
<213> ORGANISM: Bacillus subtilis

<400> SEQUENCE: 76

Tyr Lys Val Lys Ser Gly Asp Ser Leu Trp Lys Ile Ser Lys Lys Tyr
 1               5                  10                  15

Gly Met Thr Ile Asn Glu Leu Lys Lys Leu Asn Gly Leu Lys Ser Asp
                20                  25                  30

Leu Leu Arg Val Gly Gln Val Leu Lys Leu Lys
                35                  40

<210> SEQ ID NO 77
<211> LENGTH: 43
<212> TYPE: PRT
<213> ORGANISM: Bacillus subtilis

<400> SEQUENCE: 77

Tyr Lys Val Lys Ser Gly Asp Ser Leu Ser Lys Ile Ala Ser Lys Tyr
 1               5                  10                  15

Gly Thr Thr Val Ser Lys Leu Lys Ser Leu Asn Gly Leu Lys Ser Asp
                20                  25                  30

Val Ile Tyr Val Asn Gln Val Leu Lys Val Lys
                35                  40

<210> SEQ ID NO 78
<211> LENGTH: 44
<212> TYPE: PRT
<213> ORGANISM: Bacillus subtilis

<400> SEQUENCE: 78

Cys Ile Val Gln Gln Glu Asp Thr Ile Glu Arg Leu Cys Glu Arg Tyr
 1               5                  10                  15

Glu Ile Thr Ser Gln Gln Leu Ile Arg Met Asn Ser Leu Ala Leu Asp
                20                  25                  30

Asp Glu Leu Lys Ala Gly Gln Ile Leu Tyr Ile Pro
                35                  40

<210> SEQ ID NO 79
<211> LENGTH: 44
<212> TYPE: PRT
<213> ORGANISM: Escherichia coli

<400> SEQUENCE: 79

Tyr Thr Val Lys Arg Gly Asp Thr Leu Tyr Arg Ile Ser Arg Thr Thr
 1               5                  10                  15

Gly Thr Ser Val Lys Glu Leu Ala Arg Leu Asn Gly Ile Ser Pro Pro
                20                  25                  30
```

```
Tyr Thr Ile Glu Val Gly Gln Lys Leu Lys Leu Gly
            35                  40
```

<210> SEQ ID NO 80
<211> LENGTH: 44
<212> TYPE: PRT
<213> ORGANISM: Synechocystis sp.

<400> SEQUENCE: 80

```
His Val Val Lys Ala Gly Glu Thr Ile Asp Ser Ile Ala Ala Gln Tyr
  1               5                  10                  15
Gln Leu Val Pro Ala Thr Leu Ile Ser Val Asn Asn Gln Leu Ser Ser
                20                  25                  30
Gly Gln Val Thr Pro Gly Gln Thr Ile Leu Ile Pro
            35                  40
```

<210> SEQ ID NO 81
<211> LENGTH: 43
<212> TYPE: PRT
<213> ORGANISM: Bacillus subtilis

<400> SEQUENCE: 81

```
Met Val Lys Gln Gly Asp Thr Leu Ser Ala Ile Ala Ser Gln Tyr Arg
  1               5                  10                  15
Thr Thr Thr Asn Asp Ile Thr Glu Thr Asn Glu Ile Pro Asn Pro Asp
                20                  25                  30
Ser Leu Val Val Gly Gln Thr Ile Val Ile Pro
            35                  40
```

<210> SEQ ID NO 82
<211> LENGTH: 44
<212> TYPE: PRT
<213> ORGANISM: Bacillus subtilis

<400> SEQUENCE: 82

```
Tyr Asp Val Lys Arg Gly Asp Thr Leu Thr Ser Ile Ala Arg Gln Phe
  1               5                  10                  15
Asn Thr Thr Ala Ala Glu Leu Ala Arg Val Asn Arg Ile Gln Leu Asn
                20                  25                  30
Thr Val Leu Gln Ile Gly Phe Arg Leu Tyr Ile Pro
            35                  40
```

<210> SEQ ID NO 83
<211> LENGTH: 43
<212> TYPE: PRT
<213> ORGANISM: Bacillus subtilis

<400> SEQUENCE: 83

```
Ile Lys Val Lys Ser Gly Asp Ser Leu Trp Lys Leu Ala Gln Thr Tyr
  1               5                  10                  15
Asn Thr Ser Val Ala Ala Leu Thr Ser Ala Asn His Leu Ser Thr Thr
                20                  25                  30
Val Leu Ser Ile Gly Gln Thr Leu Thr Ile Pro
            35                  40
```

<210> SEQ ID NO 84
<211> LENGTH: 43
<212> TYPE: PRT
<213> ORGANISM: Bacillus subtilis

<400> SEQUENCE: 84

-continued

Tyr Thr Val Lys Ser Gly Asp Ser Leu Trp Leu Ile Ala Asn Glu Phe
1               5                   10                  15

Lys Met Thr Val Gln Glu Leu Lys Lys Leu Asn Gly Leu Ser Ser Asp
                20                  25                  30

Leu Ile Arg Ala Gly Gln Lys Leu Lys Val Ser
            35                  40

<210> SEQ ID NO 85
<211> LENGTH: 43
<212> TYPE: PRT
<213> ORGANISM: Bacillus subtilis

<400> SEQUENCE: 85

Tyr Lys Val Gln Leu Gly Asp Ser Leu Trp Lys Ile Ala Asn Lys Val
1               5                   10                  15

Asn Met Ser Ile Ala Glu Leu Lys Val Leu Asn Asn Leu Lys Ser Asp
                20                  25                  30

Thr Ile Tyr Val Asn Gln Val Leu Lys Thr Lys
            35                  40

<210> SEQ ID NO 86
<211> LENGTH: 43
<212> TYPE: PRT
<213> ORGANISM: Bacillus subtilis

<400> SEQUENCE: 86

Tyr Thr Val Lys Ser Gly Asp Ser Leu Trp Lys Ile Ala Asn Asn Tyr
1               5                   10                  15

Asn Leu Thr Val Gln Gln Ile Arg Asn Ile Asn Asn Leu Lys Ser Asp
                20                  25                  30

Val Leu Tyr Val Gly Gln Val Leu Lys Leu Thr
            35                  40

<210> SEQ ID NO 87
<211> LENGTH: 43
<212> TYPE: PRT
<213> ORGANISM: Bacillus subtilis

<400> SEQUENCE: 87

Tyr Thr Val Lys Ser Gly Asp Ser Leu Trp Val Ile Ala Gln Lys Phe
1               5                   10                  15

Asn Val Thr Ala Gln Gln Ile Arg Glu Lys Asn Asn Leu Lys Thr Asp
                20                  25                  30

Val Leu Gly Val Gly Gln Lys Leu Val Ile Ser
            35                  40

<210> SEQ ID NO 88
<211> LENGTH: 44
<212> TYPE: PRT
<213> ORGANISM: Caenorhabditis elegans

<400> SEQUENCE: 88

Thr Glu Ile Lys Ser Gly Asp Ser Cys Trp Asn Ile Ala Ser Asn Ala
1               5                   10                  15

Lys Ile Ser Val Glu Arg Leu Gln Gln Leu Asn Lys Gly Met Lys Cys
                20                  25                  30

Asp Lys Leu Pro Leu Gly Asp Lys Leu Cys Leu Ala
            35                  40

```
<210> SEQ ID NO 89
<211> LENGTH: 44
<212> TYPE: PRT
<213> ORGANISM: Caenorhabditis elegans

<400> SEQUENCE: 89

Leu Lys Leu Lys Ala Glu Asp Thr Cys Pro Lys Ile Trp Ser Ser Gln
 1               5                  10                  15

Lys Leu Ser Glu Arg Gln Phe Leu Gly Met Asn Glu Gly Met Asp Cys
            20                  25                  30

Asp Lys Leu Lys Val Gly Lys Glu Val Cys Val Ala
        35                  40

<210> SEQ ID NO 90
<211> LENGTH: 44
<212> TYPE: PRT
<213> ORGANISM: Caenorhabditis elegans

<400> SEQUENCE: 90

His Lys Ile Gln Lys Gly Asp Thr Cys Phe Lys Ile Trp Thr Thr Asn
 1               5                  10                  15

Lys Ile Ser Glu Lys Gln Phe Arg Asn Leu Asn Lys Gly Leu Asp Cys
            20                  25                  30

Asp Lys Leu Glu Ile Gly Lys Glu Val Cys Ile Ser
        35                  40

<210> SEQ ID NO 91
<211> LENGTH: 44
<212> TYPE: PRT
<213> ORGANISM: Caenorhabditis elegans

<400> SEQUENCE: 91

Leu Lys Ile Lys Glu Gly Asp Thr Cys Tyr Asn Ile Trp Thr Ser Gln
 1               5                  10                  15

Lys Ile Ser Glu Gln Glu Phe Met Glu Leu Asn Lys Gly Leu Asp Cys
            20                  25                  30

Asp Lys Leu Glu Ile Gly Lys Glu Val Cys Val Thr
        35                  40

<210> SEQ ID NO 92
<211> LENGTH: 44
<212> TYPE: PRT
<213> ORGANISM: Caenorhabditis elegans

<400> SEQUENCE: 92

Tyr Arg Phe Lys Lys Gly Asp Thr Cys Tyr Lys Ile Trp Thr Ser His
 1               5                  10                  15

Lys Met Ser Glu Lys Gln Phe Arg Ala Leu Asn Arg Gly Ile Asp Cys
            20                  25                  30

Asp Arg Leu Val Pro Gly Lys Glu Leu Cys Val Gly
        35                  40

<210> SEQ ID NO 93
<211> LENGTH: 44
<212> TYPE: PRT
<213> ORGANISM: Caenorhabditis elegans

<400> SEQUENCE: 93

Ile Thr Val Lys Pro Gly Asp Thr Cys Phe Ser Ile Trp Thr Ser Gln
 1               5                  10                  15

Lys Met Thr Gln Gln Gln Phe Met Asp Ile Asn Pro Glu Leu Asp Cys
```

```
                    20                  25                  30

Asp Lys Leu Glu Ile Gly Lys Glu Val Cys Val Thr
            35                  40

<210> SEQ ID NO 94
<211> LENGTH: 44
<212> TYPE: PRT
<213> ORGANISM: Caenorhabditis elegans

<400> SEQUENCE: 94

Val Lys Ile Asn Pro Gly Asp Thr Cys Phe Asn Ile Trp Thr Ser Gln
  1               5                  10                  15

Arg Met Thr Gln Gln Gln Phe Met Asp Leu Asn Lys Arg Leu Asp Cys
                 20                  25                  30

Asp Lys Leu Glu Val Gly Lys Glu Val Cys Val Thr
            35                  40

<210> SEQ ID NO 95
<211> LENGTH: 44
<212> TYPE: PRT
<213> ORGANISM: Caenorhabditis elegans

<400> SEQUENCE: 95

Val Gln Ile Asn Pro Gly Asp Thr Cys Phe Lys Ile Trp Ser Ala Gln
  1               5                  10                  15

Lys Leu Thr Glu Gln Gln Phe Met Glu Leu Asn Lys Gly Leu Asp Cys
                 20                  25                  30

Asp Arg Leu Glu Val Gly Lys Glu Val Cys Ile Ala
            35                  40

<210> SEQ ID NO 96
<211> LENGTH: 44
<212> TYPE: PRT
<213> ORGANISM: Caenorhabditis elegans

<400> SEQUENCE: 96

Thr Glu Val Lys Glu Gly Asp Thr Cys Phe Lys Ile Trp Ser Ala His
  1               5                  10                  15

Lys Ile Thr Glu Gln Gln Phe Met Glu Met Asn Arg Gly Leu Asp Cys
                 20                  25                  30

Asn Arg Leu Glu Val Gly Lys Glu Val Cys Ile Val
            35                  40

<210> SEQ ID NO 97
<211> LENGTH: 44
<212> TYPE: PRT
<213> ORGANISM: Caenorhabditis elegans

<400> SEQUENCE: 97

Ile Lys Val Lys Glu Gly Asp Thr Cys Phe Lys Ile Trp Ser Ala Gln
  1               5                  10                  15

Lys Met Thr Glu Gln Gln Phe Met Glu Met Asn Arg Gly Leu Asp Cys
                 20                  25                  30

Asn Lys Leu Met Val Gly Lys Glu Val Cys Val Ser
            35                  40

<210> SEQ ID NO 98
<211> LENGTH: 41
<212> TYPE: PRT
<213> ORGANISM: Caenorhabditis elegans
```

-continued

```
<400> SEQUENCE: 98

Ala Thr Ile Thr Pro Gly Asn Thr Cys Phe Asn Ile Ser Val Ala Tyr
 1               5                  10                  15

Gly Ile Asn Leu Thr Asp Leu Gln Lys Thr Tyr Asp Cys Lys Ala Leu
            20                  25                  30

Glu Val Gly Asp Thr Ile Cys Val Ser
        35                  40

<210> SEQ ID NO 99
<211> LENGTH: 44
<212> TYPE: PRT
<213> ORGANISM: Caenorhabditis elegans

<400> SEQUENCE: 99

Ile Glu Val Ile Lys Gly Asp Thr Cys Trp Phe Leu Glu Asn Ala Phe
 1               5                  10                  15

Lys Thr Asn Gln Thr Glu Met Glu Arg Ala Asn Glu Gly Val Lys Cys
            20                  25                  30

Asp Asn Leu Pro Ile Gly Arg Met Met Cys Val Trp
        35                  40

<210> SEQ ID NO 100
<211> LENGTH: 44
<212> TYPE: PRT
<213> ORGANISM: Caenorhabditis elegans

<400> SEQUENCE: 100

His Thr Ile Lys Ser Gly Asp Thr Cys Trp Lys Ile Ala Ser Glu Ala
 1               5                  10                  15

Ser Ile Ser Val Gln Glu Leu Glu Gly Leu Asn Ser Lys Lys Ser Cys
            20                  25                  30

Ala Asn Leu Ala Val Gly Leu Ser Glu Gln Glu Phe
        35                  40

<210> SEQ ID NO 101
<211> LENGTH: 44
<212> TYPE: PRT
<213> ORGANISM: Caenorhabditis elegans

<400> SEQUENCE: 101

Ile His Val Lys Glu Gly Asp Thr Cys Tyr Thr Ile Trp Thr Ser Gln
 1               5                  10                  15

His Leu Thr Glu Lys Gln Phe Met Asp Met Asn Glu Glu Leu Asn Cys
            20                  25                  30

Gly Met Leu Glu Ile Gly Asn Glu Val Cys Val Asp
        35                  40

<210> SEQ ID NO 102
<211> LENGTH: 41
<212> TYPE: PRT
<213> ORGANISM: Caenorhabditis elegans

<400> SEQUENCE: 102

Ala Thr Val Thr Pro Gly Ser Ser Cys Tyr Thr Ile Ser Ala Ser Tyr
 1               5                  10                  15

Gly Leu Asn Leu Ala Glu Leu Gln Thr Thr Tyr Asn Cys Asp Ala Leu
            20                  25                  30

Gln Val Asp Asp Thr Ile Cys Val Ser
        35                  40
```

<210> SEQ ID NO 103
<211> LENGTH: 44
<212> TYPE: PRT
<213> ORGANISM: Caenorhabditis elegans

<400> SEQUENCE: 103

Ile Glu Ile Leu Asn Gly Asp Thr Cys Gly Phe Leu Glu Asn Ala Phe
1               5                   10                  15

Gln Thr Asn Asn Thr Glu Met Glu Ile Ala Asn Glu Gly Val Lys Cys
            20                  25                  30

Asp Asn Leu Pro Ile Gly Arg Met Met Cys Val Trp
        35                  40

<210> SEQ ID NO 104
<211> LENGTH: 45
<212> TYPE: PRT
<213> ORGANISM: Bacillus subtilis

<400> SEQUENCE: 104

His Thr Val Gln Lys Lys Glu Thr Leu Tyr Arg Ile Ser Met Lys Tyr
1               5                   10                  15

Tyr Lys Ser Arg Thr Gly Glu Glu Lys Ile Arg Ala Tyr Asn His Leu
            20                  25                  30

Asn Gly Asn Asp Val Tyr Thr Gly Val Leu Asp Ile Pro
        35                  40                  45

<210> SEQ ID NO 105
<211> LENGTH: 49
<212> TYPE: PRT
<213> ORGANISM: Citrobacter freundii

<400> SEQUENCE: 105

Tyr Thr Leu Lys Thr Gly Glu Ser Val Ala Gln Leu Ser Lys Ser Gln
1               5                   10                  15

Gly Ile Ser Val Pro Val Ile Trp Ser Leu Asn Lys His Leu Tyr Ser
            20                  25                  30

Ser Glu Ser Glu Met Met Lys Ala Ser Pro Gly Gln Gln Ile Ile Leu
        35                  40                  45

Pro

<210> SEQ ID NO 106
<211> LENGTH: 49
<212> TYPE: PRT
<213> ORGANISM: Escherichia coli

<400> SEQUENCE: 106

Tyr Thr Leu Lys Thr Gly Glu Thr Val Ala Asp Leu Ser Lys Ser Gln
1               5                   10                  15

Asp Ile Asn Leu Ser Thr Ile Trp Ser Leu Asn Lys His Leu Tyr Ser
            20                  25                  30

Ser Glu Ser Glu Met Met Lys Ala Ala Pro Gly Gln Gln Ile Ile Leu
        35                  40                  45

Pro

<210> SEQ ID NO 107
<211> LENGTH: 51
<212> TYPE: PRT
<213> ORGANISM: Bacillus subtilis

<400> SEQUENCE: 107

```
Ile Glu Val Gln Gln Gly Asp Thr Leu Trp Ser Ile Ala Asp Gln Val
  1               5                  10                  15

Ala Asp Thr Lys Lys Ile Asn Lys Asn Asp Phe Ile Glu Trp Val Ala
             20                  25                  30

Asp Lys Asn Gln Leu Gln Thr Ser Asp Ile Gln Pro Gly Asp Glu Leu
         35                  40                  45

Val Ile Pro
     50
```

<210> SEQ ID NO 108
<211> LENGTH: 55
<212> TYPE: PRT
<213> ORGANISM: Streptococcus pyogenes

<400> SEQUENCE: 108

```
Tyr Thr Val Lys Tyr Gly Asp Thr Leu Ser Thr Ile Ala Glu Ala Met
  1               5                  10                  15

Gly Ile Asp Val His Val Leu Gly Asp Ile Asn His Ile Ala Asn Ile
             20                  25                  30

Asp Leu Ile Phe Pro Asp Thr Ile Leu Thr Ala Asn Tyr Asn Gln His
         35                  40                  45

Gly Gln Ala Thr Thr Leu Thr
     50                  55
```

<210> SEQ ID NO 109
<211> LENGTH: 58
<212> TYPE: PRT
<213> ORGANISM: Bacillus subtilis

<400> SEQUENCE: 109

```
Tyr Thr Val Lys Lys Gly Asp Thr Leu Trp Asp Ile Ala Gly Arg Phe
  1               5                  10                  15

Tyr Gly Asn Ser Thr Gln Trp Arg Lys Ile Trp Asn Ala Asn Lys Thr
             20                  25                  30

Ala Met Ile Lys Arg Ser Lys Arg Asn Ile Arg Gln Pro Gly His Trp
         35                  40                  45

Ile Phe Pro Gly Gln Lys Leu Lys Ile Pro
     50                  55
```

<210> SEQ ID NO 110
<211> LENGTH: 58
<212> TYPE: PRT
<213> ORGANISM: Bacillus subtilis

<400> SEQUENCE: 110

```
Tyr Thr Val Lys Lys Gly Asp Thr Leu Trp Asp Leu Ala Gly Lys Phe
  1               5                  10                  15

Tyr Gly Asp Ser Thr Lys Trp Arg Lys Ile Trp Lys Val Asn Lys Lys
             20                  25                  30

Ala Met Ile Lys Arg Ser Lys Arg Asn Ile Arg Gln Pro Gly His Trp
         35                  40                  45

Ile Phe Pro Gly Gln Lys Leu Lys Ile Pro
     50                  55
```